(12) United States Patent
Slatkine

(10) Patent No.: US 7,935,139 B2
(45) Date of Patent: May 3, 2011

(54) EYE SAFE DERMATOLOGICAL PHOTOTHERAPY

(75) Inventor: Michael Slatkine, Herzlia (IL)

(73) Assignee: Candela Corporation, Wayland, MA (US)

( * ) Notice: Subject to any disclaimer, the term of this patent is extended or adjusted under 35 U.S.C. 154(b) by 1854 days.

(21) Appl. No.: 11/005,253

(22) Filed: Dec. 6, 2004

(65) Prior Publication Data

US 2005/0147137 A1    Jul. 7, 2005
US 2010/0246619 A9   Sep. 30, 2010

Related U.S. Application Data

(63) Continuation-in-part of application No. 10/498,382, filed on Jun. 10, 2004, now Pat. No. 7,762,964, which is a continuation-in-part of application No. PCT/IL02/00635, filed on Aug. 2, 2002, and a continuation-in-part of application No. 10/614,672, filed on Jul. 7, 2003, now Pat. No. 7,184,614, application No. 11/005,253, which is a continuation-in-part of application No. PCT/IL03/00277, filed on Apr. 3, 2003.

(30) Foreign Application Priority Data

Dec. 10, 2001   (IL) .......................................... 147009
Jun. 6, 2002    (IL) .......................................... 150094
Aug. 2, 2002    (WO) ........................ PCT/IL02/00635
Sep. 11, 2002   (IL) .......................................... 151694
Feb. 22, 2004   (IL) .......................................... 160510

(51) Int. Cl.
*A61N 5/06*          (2006.01)

(52) U.S. Cl. ............................... 607/88; 607/90; 607/91
(58) Field of Classification Search ................ 606/3–12, 606/20–31; 607/88–91, 96; 128/898
See application file for complete search history.

(56) References Cited

U.S. PATENT DOCUMENTS 3,982,541 A     9/1976   L'Esperance, Jr.
4,592,353 A     6/1986   Daikuzono
(Continued)

FOREIGN PATENT DOCUMENTS
EP              761257          3/1997
(Continued)

OTHER PUBLICATIONS

Effects of Tissue Optical Clearing ,..., Lasers Light within Tissue (G. Vergas & A.J. Welch, "Laser in Surgery and Medicine", Supp. 13, 2001, p. 26).

(Continued)

*Primary Examiner* — Ahmed M Farah
(74) *Attorney, Agent, or Firm* — Proskauer Rose LLP

(57) ABSTRACT

A method and apparatus are disclosed for improving bodily safety during exposure to an intense pulsed light source by diverging the light, such as with a diffuser. At a first position of the distal end of the light source the energy density of exit light from the distal end is substantially equal to the energy density of the light required for desired applications, such as effecting an aesthetic improvement without appearance of purpura or scarring, and at a second position of the distal end the radiance of the light emitted therefrom is significantly less than the radiance of the intense pulsed light. Eye safety is further enhanced by attaching at least one element of adjustable opacity to the handpiece of the light source, so that subcutaneously backscattered light may be absorbed by the at least one element.

19 Claims, 17 Drawing Sheets

U.S. PATENT DOCUMENTS

| | | | |
|---|---|---|---|
| 4,736,743 A | 4/1988 | Daikuzono | |
| 4,976,709 A | 12/1990 | Sand | |
| 5,057,104 A | 10/1991 | Chess | |
| 5,059,192 A | 10/1991 | Zaias | |
| 5,066,293 A | 11/1991 | Furumoto | |
| 5,217,455 A | 6/1993 | Tan | |
| 5,226,907 A | 7/1993 | Tankovich | |
| 5,282,797 A | 2/1994 | Chess | |
| 5,312,395 A | 5/1994 | Tan et al. | |
| 5,344,418 A | 9/1994 | Ghaffari | |
| 5,401,270 A | 3/1995 | Muller et al. | |
| 5,411,502 A | 5/1995 | Zair | |
| 5,415,655 A * | 5/1995 | Fuller et al. | 606/16 |
| 5,429,601 A | 7/1995 | Conley et al. | |
| 5,431,647 A | 7/1995 | Purcell, Jr. et al. | |
| 5,449,354 A | 9/1995 | Konwitz et al. | |
| 5,527,308 A | 6/1996 | Anderson et al. | |
| 5,530,780 A * | 6/1996 | Ohsawa | 385/31 |
| 5,558,660 A | 9/1996 | Dreier | |
| 5,595,568 A | 1/1997 | Anderson et al. | |
| 5,626,631 A | 5/1997 | Eckhouse | |
| 5,630,811 A | 5/1997 | Miller | |
| 5,655,547 A | 8/1997 | Karni | |
| 5,735,844 A | 4/1998 | Anderson et al. | |
| 5,745,519 A | 4/1998 | Ruda et al. | |
| 5,814,041 A | 9/1998 | Anderson et al. | |
| 5,853,407 A | 12/1998 | Miller | |
| 5,871,521 A | 2/1999 | Kaneda et al. | |
| 5,879,346 A | 3/1999 | Waldman et al. | |
| 5,885,273 A | 3/1999 | Eckhouse et al. | |
| 5,947,957 A | 9/1999 | Morris | |
| 5,961,475 A | 10/1999 | Guitay | |
| 5,964,749 A | 10/1999 | Eckhouse et al. | |
| 6,011,890 A | 1/2000 | Neuberger | |
| 6,096,029 A | 8/2000 | O'Donnell, Jr. | |
| 6,120,497 A | 9/2000 | Anderson et al. | |
| 6,132,392 A | 10/2000 | Stone | |
| 6,142,650 A | 11/2000 | Brown et al. | |
| 6,149,645 A | 11/2000 | Tobinick | |
| 6,165,170 A | 12/2000 | Wynne et al. | |
| 6,185,356 B1 | 2/2001 | Parker et al. | |
| 6,197,020 B1 | 3/2001 | O'Donnell, Jr. | |
| 6,214,034 B1 | 4/2001 | Azar | |
| 6,261,310 B1 | 7/2001 | Neuberger et al. | |
| 6,264,649 B1 | 7/2001 | Whitcroft et al. | |
| 6,270,492 B1 * | 8/2001 | Sinofsky | 606/15 |
| 6,273,884 B1 | 8/2001 | Altshuler et al. | |
| 6,280,438 B1 * | 8/2001 | Eckhouse et al. | 606/9 |
| 6,508,813 B1 * | 1/2003 | Altshuler | 606/9 |
| 6,530,920 B1 | 3/2003 | Whitcroft et al. | |
| 6,544,259 B1 | 4/2003 | Tsaliovich | |
| 6,662,054 B2 | 12/2003 | Kreindel et al. | |
| 6,663,620 B2 | 12/2003 | Altshuler et al. | |
| 6,902,554 B2 | 6/2005 | Huttner | |
| 7,083,610 B1 | 8/2006 | Murray et al. | |
| 7,108,689 B2 | 9/2006 | Eckhouse et al. | |
| 7,184,614 B2 * | 2/2007 | Slatkine | 385/5 |
| 2002/0012860 A1 | 1/2002 | Yoo | |
| 2002/0034012 A1 | 3/2002 | Santoro et al. | |
| 2002/0128600 A1 | 9/2002 | Nissels | |
| 2002/0128635 A1 | 9/2002 | Altshuler et al. | |
| 2002/0169442 A1 | 11/2002 | Neev | |
| 2003/0083536 A1 | 5/2003 | Eshel et al. | |
| 2004/0077977 A1 | 4/2004 | Ella et al. | |
| 2004/0082940 A1 | 4/2004 | Black et al. | |
| 2004/0254599 A1 | 12/2004 | Lipoma et al. | |
| 2005/0251117 A1 | 11/2005 | Anderson et al. | |
| 2005/0251118 A1 | 11/2005 | Anderson et al. | |
| 2005/0261584 A1 | 11/2005 | Eshel et al. | |
| 2006/0013533 A1 | 1/2006 | Slatkine | |
| 2006/0189964 A1 | 8/2006 | Anderson et al. | |
| 2006/0211958 A1 | 9/2006 | Rosenberg et al. | |
| 2006/0241573 A1 | 10/2006 | Roersma et al. | |
| 2007/0027411 A1 | 2/2007 | Ella et al. | |
| 2007/0179482 A1 | 8/2007 | Anderson | |
| 2007/0230520 A1 | 10/2007 | Mordaunt et al. | |

FOREIGN PATENT DOCUMENTS

| | | |
|---|---|---|
| EP | 0880940 B1 | 2/1998 |
| EP | 0 880 940 A2 | 12/1998 |
| EP | 933096 | 8/1999 |
| EP | 1 031 324 | 8/2000 |
| EP | 1116476 | 7/2001 |
| EP | 1 168 535 | 1/2002 |
| JP | 2001-212231 | 8/2001 |
| JP | 2005-087520 | 4/2005 |
| WO | WO 99/27863 A1 | 6/1999 |
| WO | WO 99/46005 | 9/1999 |
| WO | WO 00/60711 | 10/2000 |
| WO | WO 00/72771 A1 | 12/2000 |
| WO | WO 2004004803 A2 | 1/2004 |

OTHER PUBLICATIONS

W. Kapit et al., *The Physiology Coloring Book*, Harper Collins Publishers, 1987, pp. 88-89.

International Search Report for International Application No. PCT/IL2002/00635, Date of Mailing Feb. 28, 2003 (5 pages).

International Search Report for International Application No. PCT/IL2003/00277, Date of Mailing Nov. 5, 2003 (1 page).

Office Action for U.S. Appl. No. 10/498,382, Date of Mailing Mar. 18, 2009 (5 pages).

Office Action for U.S. Appl. No. 10/498,382, Date of Mailing Jun. 30, 2008 (6 pages).

Office Action for U.S. Appl. No. 11/229,983, Date of Mailing Sep. 3, 2008 (7 pages).

Office Action for U.S. Patent No. 7,184,614 (U.S. Appl. No. 10/614,672) Date of Mailing Dec. 15, 2005 (6 pages).

Office Action for U.S. Patent No. 7,184,614 (U.S. Appl. No. 10/614,672) Date of Mailing Jan. 30, 2006 (6 pages).

* cited by examiner

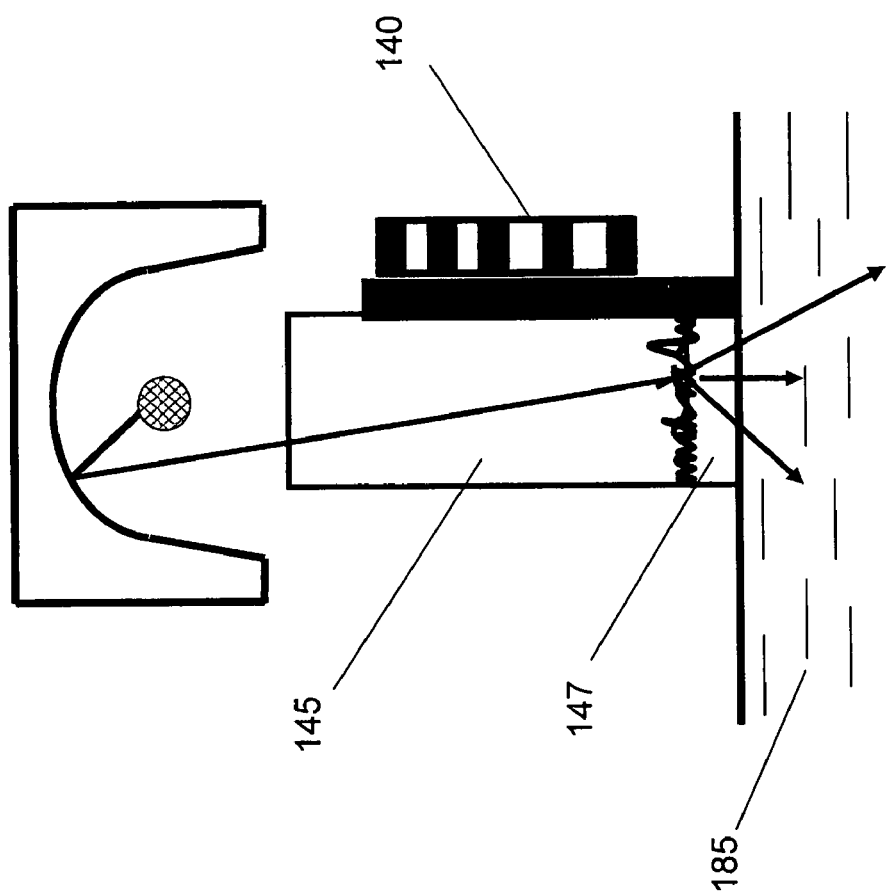

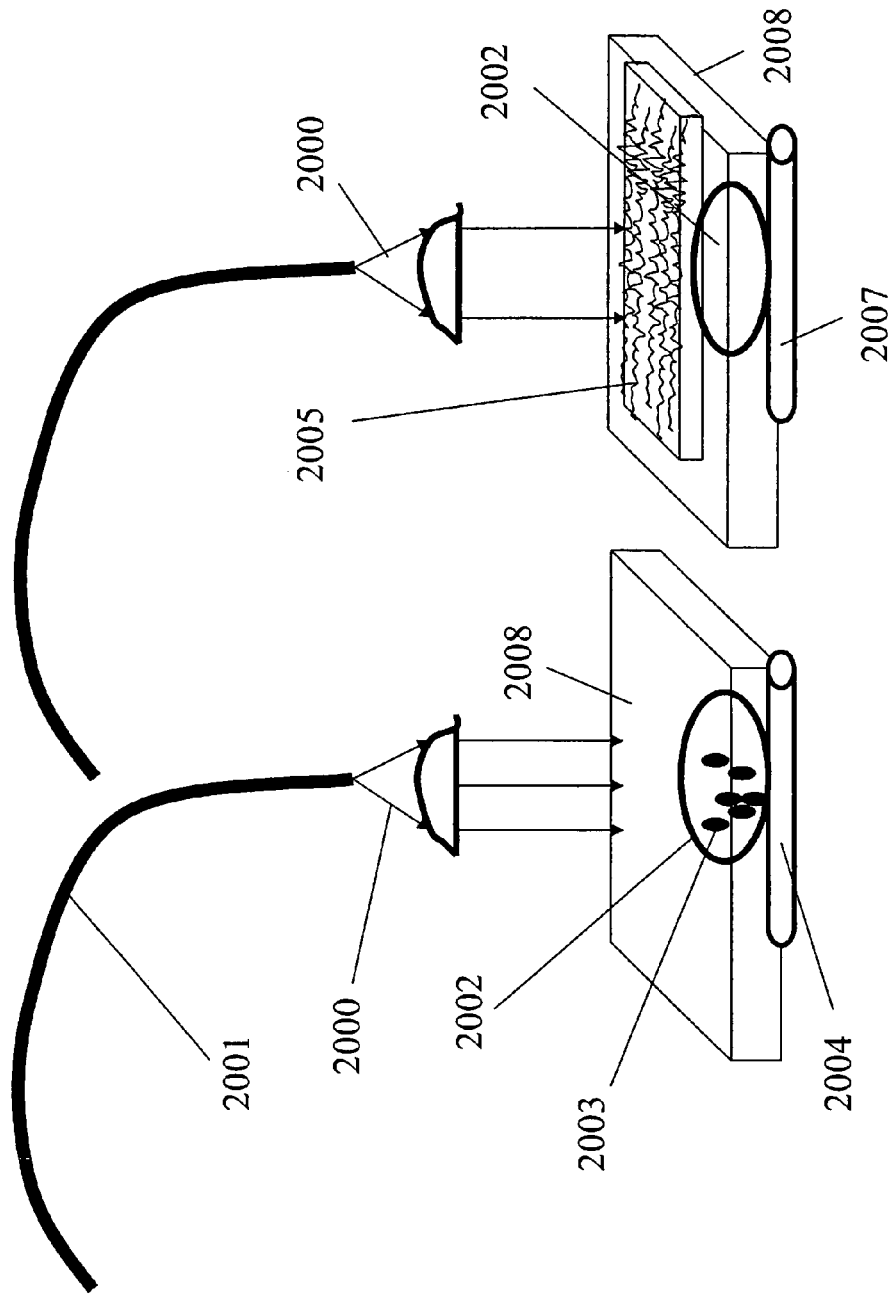

EYE SAFE DERMATOLOGICAL PHOTOTHERAPY

CROSS REFERENCE TO RELATED APPLICATIONS

This application is a continuation-in-part of international application no. PCT/IL03/00277 (filed on Apr. 3, 2003), which claims priority from Israeli patent application no. 150094 (filed on Jun. 6, 2002), international application no. PCT/IL02/00635 (filed on Aug. 2, 2002) and Israeli patent application no. 151694 (filed on Sep. 11, 2002). This application is also a continuation-in-part of U.S. application Ser. No. 10/498,382 (filed on Jun. 10, 2004), the contents of all of which are incorporated herein by reference. U.S. application Ser. No. 10/498,382 is a continuation-in-part of international application no. PCT/IL02/00635 (filed on Aug. 2, 2002), which claims the benefit of and priority to Israeli patent application no. 147009 (filed on Dec. 10, 2001) and Israeli patent application no. 150094 (filed on Jun. 6, 2002). U.S. application Ser. No. 10/498,382 is also a continuation-in-part of U.S. application Ser. No. 10/614,672, filed Jul. 7, 2003, now U.S. Pat. No. 7,184,614. U.S. application Ser. No. 10/498,382 also claims the benefit of and priority to Israeli patent application no. 160510 (filed on Feb. 22, 2004).

FIELD OF THE INVENTION

The present invention is related to the field of intense pulsed light sources. More particularly, the present invention is related to providing an eye-safe, intense pulsed light source that is suitable for correcting aesthetic skin disorders that require a very high energy density. Even more specifically, the present invention is related to a method and apparatus for improving bodily safety during exposure to an intense pulsed light source, by diverging the intense pulsed light which provides the required energy density of light for desired applications at a very short distance, but is inherently safe to the eyes of bystanders.

BACKGROUND OF THE INVENTION

Intense Pulsed Light (IPL) sources are used for the treatment of a variety of aesthetic skin problems, including hair removal, skin rejuvenation including wrinkle removal, treatment of vascular lesions, treatment of acne, etc. Intense pulsed light sources are broad band sources, such as Xenon flash lamps, spectrally filtered to obtain narrower and more selective emission wavelengths. Typical energy density levels utilized in hair removal are 5-50 J/cm$^2$, with pulse durations ranging from approximately 3 to 300 msec. IPL sources are mostly operated in a multiple pulse train mode such as a 50 msec pulse which consists of three pulses of 3 msec each with a 20 msec delay between the pulses. The treatment area is often close to 1×4 cm.

Such treatment is generally conducted by trained personnel, such as nurses under the supervision of a physician. Aesthetic systems based on high intensity light are divided into monochromatic pulsed laser sources, such as described in U.S. Pat. No. 5,879,346 and non-coherent broad-band IPL sources, such as described in U.S. Pat. Nos. 5,683,380, 5,885,273, 6,187,001, 6,280,438, 6,214,034, 5,964,749, and 6,387,089.

These prior art systems are extremely risky to the eyes and may cause blindness if a bystander or a patient accidentally stares at the distal end of the treatment system. As a result, the safety level of prior art laser and IPL sources utilized for aesthetic treatments is such that protective eyeglasses are mandatory. The use of both laser and IPL sources without supervision of a physician is prohibited in many countries.

In addition to the accidental risk associated with directly staring at the distal end of a pulsed light based treatment device without wearing protective eyeglasses, there is a longer term risk associated with unavoidable staring at the treatment site. The treated skin backscatters bright light which originates from the treatment device, and the backscattered light repeatedly reaches the eyes of an operator, causing severe eye fatigue.

The conversion of an IPL aesthetic source into an inherently eye-safe device which does not require medically trained operators and which does not necessitate the use of inconvenient protective eyeglasses would therefore be advantageous. Protective eyeglasses, which are needed for the attenuation of backscattered treatment light and should transmit ambient illuminating light having a broad band spectrum for adequate visibility, limit the field of view of an operator and are opaque at a broad range of wavelengths, resulting in a darkened treatment site.

The need for protective eyeglasses during aesthetic treatments is obviated if the risks associated with direct staring at the distal end of an IPL source and with skin backscattering are eliminated. Co-pending International Patent Publication WO 03/049633 by the same applicant, the description of which is incorporated herein by reference, discloses a laser unit suitable for aesthetic treatment, which is converted into an eye-safe laser unit.

One cause of eye risk associated with aesthetic treatments with a non-coherent IPL source is the possibility of staring directly at the flash lamp through a light guide (see FIG. 2). When a light guide is not employed, as described in U.S. Pat. No. 6,187,001, direct view is even more probable. The energy density emitted directly from a flash lamp, e.g. having a size of 3×40 mm, may reach an energy density level of 40-60 J/cm$^2$ or higher. The flash lamp may be considered a diffused light source which emits energy at a solid angle close to 3.14 steradians, achieved by ideal diffuser sources with 100% transmission and provided with Lambertian angular scattering properties. As a result, the radiance, i.e. the energy density per solid angle, of the flash lamp is close to 15-20 J/cm$^2$/steradian. In many cases radiance may be even higher than that level. The maximal permitted radiance or accessible emission limit (AEL) emitted from an extended diffused light source used without protective eyeglasses is given in the FDA eye safety standard 1040.10 21 CFR Ch.1 and in the ANSI Z136.1 standard, and is a function of wavelength and pulse duration. If divided into narrow spectral segments, the radiance for each spectral segment is given by the equation: AEL=10*k1*k2*T^⅓, where k1 equals 1 in the visible part of the spectrum, 1.6 at a wavelength of approximately 800 nm, 3 at a wavelength of approximately 980 nm and 5 at a wavelength of approximately 1064 nm, k2=1, and T is the pulse duration expressed in seconds.

Most intense pulsed light sources operate in spectral bands having a lower limit of approximately 585 nm (k1=1) or 645 nm wavelength (k1=1) for photorejuvenation and 755 nm (k1=1.3) or 810 wavelength (k1=1.6) for hair removal. The energy content at a higher wavelength is smaller. As a result, the maximal permitted radiance from IPL sources approximates AEL=10*1.5*T^⅓. For a pulse duration of 3 msec often used for photorejuvenation, which is strongly based on absorption of light in extremely thin vessels with a thermal relaxation time of less than 1 msec, the AEL is approximately 3 J/cm$^2$/sr, a value much less than the radiance emitted by a flash lamp of 15-20 J/cm$^2$/sr, as referred to hereinbefore. An IPL source used with high efficacy in aesthetic treatments is therefore not eye-safe and emits a radiance which may be 6-13 times above the safe limit set by the aforementioned FDA standard. It will be appreciated that even a factor of 2 above the accepted standard for eye safety requires the use of inconvenient protective glasses during an aesthetic treatment.

It will be appreciated that there is a trade off between the efficacy of an intense light source used in aesthetic treatments and the corresponding eye or skin safety. As the efficacy is higher, the energy density is higher, and therefore there is a higher risk of burning the skin since such an intense light source is in contact with the skin. To prevent skin burning, some prior art intense light sources are provided with a chiller, which chills the skin just before firing the IPL.

Although a variety of IPL sources are used in the treatment of aesthetic skin disorders such as devices produced by LUMENIS USA (Epilight, Quantum), RADIANCY, PALOMAR (USA), DEKA (ITALY), SYNERON (Israel), and the fluorescent frequency-shifted PLASMALITE™ (USA, SWEDEN), they all suffer from the high risk associated with the existence of a direct line of sight between a flash lamp and the eye. Furthermore, prior art aesthetic systems which utilize high energy, short pulse duration flash lamps for hair removal, wrinkle removal, skin rejuvenation or the treatment of acne, lack protective measures, such as a light diffuser placed within the line of sight between the flash lamp and skin, which would obviate the use of protective eyeglasses during the treatment.

As mentioned above, in order to completely eliminate the necessity of wearing inconvenient protective eyeglasses during aesthetic treatments with IPL sources, the amount of backscattered treatment light which reaches the eyes should also be reduced.

Protective eyeglasses used in conjunction with IPL sources, such as those produced by Glendale USA, Laser-R Shield USA, Bolle, France, or Yamamoto, Japan are generally based on selective absorption of light by an optical filter. Since the protective eyeglasses used to reduce broad band radiation associated with IPL sources are dark, the visibility of the treatment site, which is usually illuminated by broad band radiation, is similarly reduced. Other protective eyeglasses, such as those disclosed in U.S. Pat. Nos. 4,462,661, 5,671,035, 5,022,742, 5,841,507, 5,519,522, 4,968,127, 5,208,688 and 6,170,947, are based on the attenuation of light by liquid crystal devices. These prior art devices are relatively heavy and cumbersome, and limit the field of view of an operator.

Additional aesthetic systems related to the current invention are devices incorporating both IPL and laser sources in a single system. For example, a "Quantum" system produced by LUMENIS incorporates a spectrally broad-band, non-coherent IPL source for hair removal or photorejuvenation and a monochromatic coherent Nd:YAG pulsed laser operated at 1064 nm for the treatment of leg veins. Coherent laser sources, like all prior art aesthetic lasers, are extremely risky to the eyes, having a radiance which is often more than 10,000 times above the AEL.

Other relevant prior art is disclosed in U.S. Pat. Nos. 5,595,568, 5,879,346, 5,226,907, 5,066,293, 5,312,395, 5,217,455, 4,976,709, 6,120,497, 5,411,502, 5,558,660, 5,655,547, 5,626,631, 5,344,418, 5,964,749, 4,736,743, 5,449,354, 5,527,308, 5,814,041, 5,595,568, 5,735,844, 5,057,104, 5,282,797, 6,011,890, 5,745,519, and 6,142,650.

If the eye safety level of a laser and of an IPL source were reduced to a level below that listed in the aforementioned standards, such a device would be able to be operated by personnel without any medical background, such as aestheticians, and also by individual users at home.

Prior art IPL sources used for aesthetic treatments are incapable of generating non-coherent light at both a high enough energy density, which would assure treatment efficacy, and at a low enough radiance, which would not present a risk of injury to the eyes of bystanders.

Subcutaneous regions commonly referred to as "hot spots," at which the treatment energy density is much higher than the average surrounding energy density, often cause a side effect during various types of aesthetic treatments such as the treatment of vascular lesions, particularly port wine stain, or the treatment of fine wrinkles in non-ablative photorejuvenation. A noticeable side effect during the treatment of port wine stain is purpura, characterized by dark spots of severely damaged vessels which remain for a few days. A noticeable side effect caused by hot spots during the treatment of wrinkles is the coagulation of collagen zones, which may result in scarring.

With respect to laser sources, such as Dye lasers which are most commonly used for the treatment of vascular lesions (although KTP, diode and Nd:YAG lasers are also used and such side effects are also noticeable therewith), the hot spots generally result from small interference speckles. With respect to IPL sources, instabilities in the arc which generates light in the flash lamp may be responsible for the hot spots.

It would be therefore be desirable to prevent the appearance of purpura during the treatment of vascular lesions or of scarring during the non-ablative treatment of wrinkles. It would be likewise be desirable to prevent the formation of inhomogeneous hot spots under the skin surface during light-based aesthetic treatments.

Co-pending U.S. patent application Ser. No. 10/498,382 by the same applicant discloses a method and apparatus for preventing the appearance of purpura, by which a controlled vacuum is applied to a vacuum chamber in contact with a skin target, so that a significantly lower energy density level relative to prior art methods is sufficient for achieving the coagulation of blood vessels. It would be desirable to prevent the occurrence of purpura without need of having to generate a vacuum.

It is an object of the present invention to provide a non-coherent IPL source that may be used for aesthetic procedures.

It is an object of the present invention to provide a non-coherent IPL source that overcomes the disadvantages of the prior art.

It is another object of the present invention to provide an IPL source that is not injurious to the eyes of an operator or of an observer located in the vicinity of, or at a distance from, a target.

It is yet another object of the present invention to provide an IPL source which does not necessitate the use of protective eyeglasses, without causing severe eye fatigue.

It is yet another object of the present invention to provide an IPL source which could be operated by personnel without any medical background.

It is a further object of the present invention to prevent the appearance of purpura during the treatment of vascular lesions with a laser or IPL source, or of scarring during the non-ablative treatment of wrinkles.

It is a further object of the present invention to prevent the formation of multiple inhomogeneous hot spots under the skin surface during light-based aesthetic treatments.

Other objects and advantages of the invention will become apparent as the description proceeds.

SUMMARY OF THE INVENTION

The present invention comprises a method of improving bodily safety of bystanders exposed to an intense pulsed light directed to a target, comprising: providing a source for generating intense pulsed light, causing said source to generate at least one pulse of polychromatic light, directing said pulsed light to a target, and diverging said pulsed light at a diverging location between said source and said target, whereby the energy density of light exiting from said diverging location is substantially equal to the energy density of the intense pulsed light, and at a distance from said diverging location the radiance of said exiting light is significantly less than the radiance of the intense pulsed light.

As referred to herein, "intense pulsed light" is defined as polychromatic light delivered by at least one pulse, which may be supplemented by energy at radio frequencies being directed at the target simultaneously with said light. Likewise an "intense pulsed light source" is defined as an instrument that generates said intense pulsed light or fluorescent pulsed light (FPL), wherein said instrument may comprise an optical frequency shifter for shifting the wavelength of the pulsed light being directed to the target.

Preferably, said pulsed light source is provided with an assembly connected to the light source, for directing said light to said target, which assembly will be called the light propagation assembly and the diverging location is the distal end of said propagation assembly. Also preferably, a scattering unit is provided at said diverging location, said unit comprising at least one scattering element, also called hereinafter "diffuser," wherein each of said scattering elements or diffusers is transparent to said intense pulsed light. As this term is used herein, "scattering" means randomly changing the direction of adjacent light beams so that they randomly diverge from one another, without any substantial change in the wavelength of the incident light. Scattering is typically caused, and is caused in the present invention, by the structure of a medium through which the light propagates.

As referred to herein, "distal" means a location closer to a target, and therefore more distant from the light source; "proximate" means a location more distant from a target, and therefore closer to the light source; "axial" means a direction from the center of the light source to the center of the target; and "transversal means a direction perpendicular to the axial direction. Therefore, if the propagation assembly is so placed that the diverging location is close to a first target, light having substantially the energy density of the generated pulsed light will impinge on said first target, but light having a significantly reduced radiance will impinge on a second target that is farther away from said diverging location. If the first target is the intended target of an optical treatment and the second target is an object that might be hurt by the intense pulsed light, the method of the invention will combine the effectiveness of the optical treatment while protecting objects that are not the intended targets of the treatment. Hereinafter, it will be said that the distal end of the propagation assembly is "in the first position" with respect to a target close to said assembly, typically the intended target of an optical treatment, and "in the second position" with respect to an object distanced from said assembly, typically an object that might be hurt by the intense pulsed light.

In another aspect, the method further comprises:
a) providing a diffusing unit transparent to the intense pulsed light comprising at least one angular beam expander and at least one diffuser;
b) attaching said diffusing unit to the distal end of the propagation assembly of the intense pulsed light source (hereinafter, briefly, the propagation assembly); and
c) allowing the intense pulsed light to propagate through said at least one angular beam expander and said at least one diffuser, whereby to scatter said intense pulsed light.

The energy density of the intense pulsed light at the first position (as hereinbefore defined) of the distal end of the propagation assembly ranges from 1 to 100 J/cm².

In one aspect, said first position is in contact with a target to which the intense pulsed light is directed.

The radiance of the divergent intense pulsed light at the second position of the distal end of the propagation assembly (as hereinbefore defined) is less than $10*k1*k2*(t^{1/3})$ J/cm²/sr, where k2=1 and t is pulse duration of the intense pulsed light in seconds, k1=1 for a wavelength ranging from 400 to 700 nm, k1=1.3 for a wavelength of approximately 570 nm, k1=1.6 for a wavelength of approximately 830 nm, k1=3 for a wavelength of approximately 940 nm, and k1=5 for a wavelength greater than 1050 nm.

The wavelength of the intense pulsed light ranges from 400 to 1300 nm. The duration of a pulse of the intense pulsed light ranges from 100 microseconds to 1000 msec.

The intense pulsed light source is placed with its propagation assembly at the first position for applications selected from the group of hair removal, skin rejuvenation, wrinkle removal, treatment of vascular lesions, treatment of pigmented skin, treatment of acne, treatment of herpes, treatment of psoriasis and tattoo removal.

In another preferred embodiment, the method of improving bodily safety of bystanders, according to the invention, further comprises the steps of providing at least one element of adjustable opacity attached to a handpiece of the intense pulsed light source, placing said handpiece at a position in close proximity with said target, increasing the opacity of said at least one element, generating light from said source, allowing light rays to propagate through the skin and to be backscattered, and allowing said backscattered light to be absorbed by said at least one element.

As referred to herein, "handpiece" means a hand-held element having an elongated, or any other suitable, shape, from which intense pulsed light exits and which facilitates directing the intense pulsed light to a desired target. Said handpiece is adapted to house the intense pulsed light source, propagation assembly, and any control system needed for optimal operation of the invention.

Preferably, the opacity of the at least one element is increased synchronously with, or shortly before, the generation of the light and is decreased following the generation of the light, whereby the skin is visible during those periods when light is not emitted by the source. The activation time of the at least one element is up to 1000 milliseconds and the deactivation time is less than 100 milliseconds.

In one aspect, the at least one element is attached externally to the handpiece. The inclination of the at least one element relative to the handpiece is preferably adjusted, in response to an instantaneous position of a bystander.

In another aspect, the visibility of the skin is increased by activating a supplementary light source.

The present invention also comprises an apparatus comprising an intense pulsed light source, for improving bodily safety of bystanders exposed to the light generated by said source, comprising a handpiece, a propagation assembly for directing the light of said source, contained within said handpiece, means attached to said guide assembly, said means adapted to increase divergence of the intense pulsed light at a given distance between the source and a target, whereby at a first position of the distal end of said propagation assembly in close proximity with said target the energy density of an exit beam from said distal end is substantially equal to the energy density of the intense pulsed light and at a second position more distant than said first position from said target the radiance of the light emitted from said distal end is significantly less than the radiance of the intense pulsed light.

In one preferred embodiment, the diverging means is also a scattering means.

In one aspect, the scattering means comprises a diffusing unit attachable to the distal end of the guide assembly of the intense pulsed light source, said diffusing unit including at least one diffuser that is transparent to the intense pulsed light.

In one aspect, the scattering means comprises a diffusing unit attachable to the distal end of the propagation assembly of the intense pulsed light source, said diffusing unit being selected from the group of at least one angular beam expander, at least one micro-prism and at least one diffuser, or a combination thereof.

The diffusing unit is preferably disposed between the intense pulsed light source and the distal end of the propagation assembly.

In one aspect, the first position is substantially in contact with a target to which the intense pulsed light is directed.

In one aspect, a coupler is disposed between the distal end of the propagation assembly and the target.

In one aspect, the apparatus further comprises a mirror disposed between the distal end of the propagation assembly and the target, said mirror preventing direct view of the source.

The energy density at the first position of the distal end of the propagation assembly ranges from 1 to 100 J/cm$^2$, the pulse duration ranges from 100 microseconds to 1000 milliseconds, and the wavelength of the intense pulsed light ranges from 400 nm to 1300 nm.

In one aspect, the apparatus further comprises a means for skin cooling, said skin cooling means being adapted to cool the diffusing unit at the first position of the distal end of the propagation assembly.

In one preferred embodiment, the apparatus further comprises a dual optical generation system said dual system being operative to controllably generate either monochromatic light or broad band intense pulsed light, comprising an apparatus for improving bodily safety of bystanders exposed to a monochromatic light source, comprising a means attached to the distal end of the propagation assembly of a monochromatic light source, said means adapted to cause the monochromatic light to be divergent, whereby at a first position of said distal end relative to a target the energy density of an exit beam from said distal end is substantially equal to the energy density of the monochromatic light and at a second position of said distal end relative to a target the energy radiance of the light emitted from said distal end is significantly less than the energy radiance of the monochromatic light, said dual system being operative to controllably generate monochromatic light and/or intense pulsed light.

The diverging means of the monochromatic light or of the intense pulsed light is preferably a scattering means which comprises a diffusing unit attachable to the distal end of the propagation assembly, said diffusing unit including at least one diffuser that is transparent to the light.

The diffuser is preferably produced such that any area thereof with a diameter of 0.75 mm scatters impinging light rays to such a degree that said area functions as an extended diffused light source when viewed from a distance of 200 mm. The diffuser is made from a material selected from the group of sapphire, glass and polycarbonate.

Preferably, the diffuser has a first diffusive face and a second smooth face in opposed relation to said first face, the diffuser being attached to the distal end of the propagation assembly in such a way that said second face is distal with respect to said first face.

In another preferred embodiment, the invention provides an eye safe handpiece, comprising:
a) a handpiece body for transmitting intense pulsed light through a distal end of said body to a target, said distal end being positionable at a predetermined location substantially in contact with said target;
b) light delivery means for delivering said light from an intense pulsed light source to said distal end;
c) means for directing the light which is transmitted through said distal end to said target; and
d) a diffusing unit attachable to said body, said diffusing unit including at least one diffuser that is transparent to said light wherein a diffusing surface of said diffuser is disposed internally to said handpiece body;
wherein the energy density of the light exiting said distal end at said location ranges from 1 to 100 J/cm$^2$,
wherein the radiance of the light exiting said distal end at said location is less than $10*k1*k2*(t^{1/3})$ J/cm$^2$/sr, where t is a pulse duration of the intense pulsed light in seconds, k2=1, k1=1 for a wavelength ranging from 580 to 700 nm, k1=1.3 for a wavelength of approximately 570 nm, k1=1.6 for a wavelength of approximately 830 nm, k1=3 for a wavelength of approximately 940 nm, and k1=5 for a wavelength greater than 1050.

Preferably—
a) the target is a skin target;
b) the diffuser has a proximal face and a distal face, the proximal face being a diffusing surface;
c) the wavelength of the intense pulsed light ranges from 400 to 1300 nm;
d) the pulse duration of the intense pulsed light ranges from 100 microseconds to 1000 msec; and
e) the handpiece is suitable for effecting an aesthetic improvement.

In another preferred embodiment, the invention is directed a method for effecting purpura-free and scar-free treatment of skin, comprising:
a) attaching a diffusing unit to the distal end of a light propagation assembly of a laser or intense pulsed light source;
b) positioning the distal end of said light propagation assembly at a predetermined location substantially in contact with a skin target;
c) setting the wavelength and energy density of the light exiting the distal end at a level which is suitable for effecting a desired treatment of said skin target;
d) firing the light source at said set wavelength and energy density level for a sufficient period of time to effect said treatment; and
e) allowing said light to be completely scattered by means of said diffusing unit, whereby said treatment is effected without formation of purpura or scarring in the vicinity of said skin target.

The invention also provides a method for preventing the appearance of purpura or scarring during treatment of a desired skin target by a laser or IPL source, comprising:
a) attaching a diffusing unit to the distal end of a light propagation assembly of a laser or intense pulsed light source;

b) positioning the distal end of said light propagation assembly at a predetermined location substantially in contact with a skin target; and c) firing the light source, while allowing the light exiting said light propagation assembly to be completely scattered by means of said diffusing unit, whereby a desired treatment is effected without formation of purpura or scarring in the vicinity of said skin target.

The invention also provides an apparatus for effecting purpura-free and scar-free treatment of skin, comprising:

a) a laser or intense pulsed light source;

b) a light propagation assembly for directing light of said source and which is displaceable to a predetermined location substantially in contact with a skin target;

c) a diffusing unit attachable to the distal end of said light propagation assembly, light exiting said light propagation assembly capable of being completely scattered by means of said diffusing unit; and d) means for setting the wavelength and energy density of the light exiting the distal end at a level which is suitable for effecting a desired treatment of said skin target without formation of purpura or scarring in the vicinity of said skin target, said completely scattered light preventing formation of purpura or scarring.

In one aspect, the laser is selected from the group of a pulsed Dye laser, a KTP laser, a diode laser, and an Nd:YAG laser.

In one aspect, the IPL is capable of emitting light in any spectral band ranging from 570 to 900 nm.

In another preferred embodiment, the apparatus for improving bodily safety of bystanders, according to the invention, comprises at least one element of adjustable opacity externally attached to a handpiece of the intense pulsed light source and so positioned so as to absorb substantially most of the subcutaneously backscattered light resulting from the generation of said intense pulsed light directed to a skin target.

In one aspect, the opacity of said at least one element is adjustable upon generation of said light.

The element is selected from the group of a liquid crystal window, a spectral density filter, an attenuation filter, a mechanical shutter, or a combination thereof.

The opacity of a density filter is preferably a predetermined constant value in accordance with the spectrum of intense pulsed light.

In one aspect, the apparatus further comprises control circuitry for synchronizing the opacity adjustment of the at least one element, in response to the generation of the light. The control circuitry is operative to cause the at least one element to be substantially transparent during those periods when light is not emitted by the source.

In another aspect, the apparatus further comprises a supplementary light source externally attached to a handpiece of the intense pulsed light for increasing skin visibility.

In one aspect, the attenuation filter is an optical band pass filter. The wavelength of the light that passes through the filter preferably is based on the chromophore of a lesion to be treated by the light.

In another aspect, the attenuation filter is a spectral filter which blocks the backscattered light and transmits the supplementary light.

The present invention is also directed to a method of aesthetic improvement, comprising:

a) providing a source for generating intense pulsed light and a light propagation assembly by which said light is directed to a target;

b) positioning the distal end of said propagation assembly at a first position in close proximity with said target;

c) causing said source to generate at least one pulse of polychromatic light;

d) diverging said pulsed light at a location between said source and said target, whereby at said first position the energy density of light exiting from said diverging location is substantially equal to the energy density of the intense pulsed light; and e) effecting an aesthetic improvement, wherein the radiance of the light emitted from said diverging location, at a second position distant from said target, is less than $10*k1*k2*(t^{1/3})$ J/cm$^2$/sr, where $k2=1$ and $t$ is pulse duration of the intense pulsed light in seconds, $k1=1$ for a wavelength ranging from 400 to 700 nm, $k1=1.3$ for a wavelength of approximately 570 nm, $k1=1.6$ for a wavelength of approximately 830 nm, $k1=3$ for a wavelength of approximately 940 nm, and $k1=5$ for a wavelength greater than 1050 nm.

In one aspect, the energy density is at least 1 J/cm$^2$ at the first position.

In one aspect, the aesthetic improvement is selected from the group of hair removal, skin rejuvenation, wrinkle removal, treatment of vascular lesions, treatment of pigmented skin, treatment of acne, treatment of herpes, treatment of psoriasis and tattoo removal.

In another aspect, the aesthetic improvement is self-effected without use of protective eyeglasses. During a self-effected aesthetic improvement, a patient positions the diverging location in close proximity to his skin, holds a handpiece of the light source, and generates the light while viewing and selecting areas of the aesthetic improvement.

BRIEF DESCRIPTION OF THE DRAWINGS

In the drawings:

FIGS. 5a-c schematically illustrate different configurations of devices adapted to conduct heat from a heated diffuser, following the generation of an intense pulsed light source, in accordance with the present invention;

FIGS. 10a-b are schematic drawings of a skin target impinged by intense pulsed light which was emitted from the distal end of an IPL source without and with a diffuser, respectively, showing the reduced appearance of purpura that may be realized with the use of the present invention.

DETAILED DESCRIPTION OF PREFERRED EMBODIMENTS

The present invention is a device for improving bodily safety during exposure to an intense pulsed light (IPL) source, which device is adapted to diffuse the intense pulsed light, the diffused light providing the required energy density of light for desired applications at a very short distance but being inherently safe to the eyes of bystanders.

In a first embodiment, the IPL source is provided with a diffusing unit which causes the light exiting from said unit to be scattered. The exit light is scattered to such a degree that the radiance of said exit light is less than the accessible emission limit (AEL), and therefore is not injurious to the eyes of bystanders that are in a direct line of view thereto.

Figure 1:
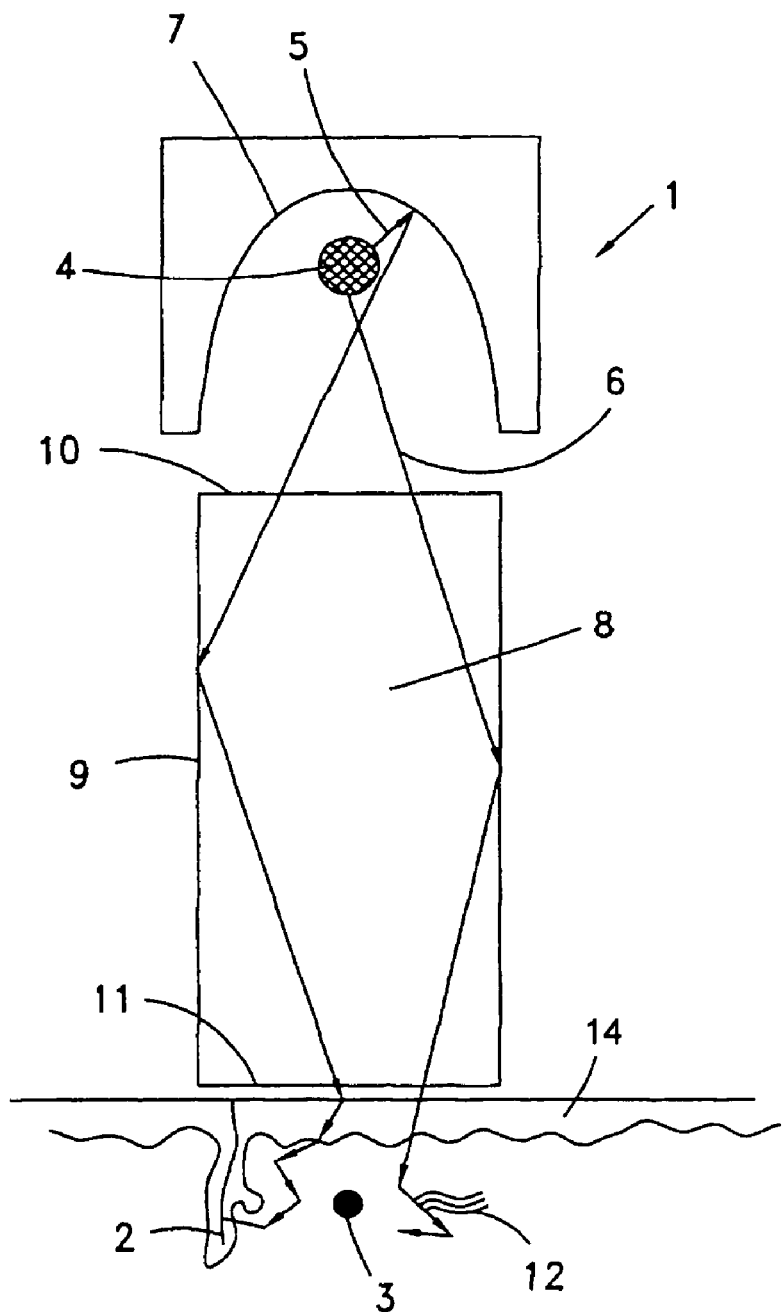
FIG. 1 is a schematic drawing of a prior art intense pulsed light source.

FIG. 1 illustrates a prior art intense pulsed light source designated generally as 1, as disclosed in U.S. Pat. Ser. No. 5,683,380, which is suitable for aesthetic treatments at a target skin location 14. IPL source comprises high intensity pulsed flash lamp 4, which generates polychromatic light, and light guide 8. Generated light rays such as 5 and 6 are either reflected from reflector 7 into light guide 8 or propagate directly through light guide 8 without any intermediate reflection. The light energy is transmitted through the light guide and may be reflected by wall 9 of the light guide towards the skin. The light exits light guide 8 through distal end 11 thereof, which is planar and transparent to the non-coherent light. Distal end 11 is generally placed in contact with target skin location 14, or is extremely close thereto. The light impinges the skin with a minimal loss in energy density and due to the extremely small spacing between the distal end 11 and skin 14. The light energy which propagates through the skin is scattered to a large degree within the skin and just a small fraction thereof reaches hair follicles 2, blood vessels 3 or collagen bundles 12. Concerning hair follicles, for example, the scattered light impinges and destroys a hair strand contained within a given follicle. Intense pulsed light sources are broad band sources, resulting in the absorption of a percentage of the energy, for example, in one part of the spectrum by melanin in hair filaments and a percentage of the energy in another part of the spectrum by blood vessels.

The selected spectral band and pulse duration of the IPL source depend on the specific application. The energy density of the IPL source at distal end 11 of the light guide, or upon impinging skin 14, has to be above a predetermined threshold level in order to be efficacious. For example, IPL sources are operated at a relatively high energy density of 7-55 $J/cm^2$ for hair removal. Some systems utilize trains of 2-3 pulses, with each pulse having a duration of approximately 2.5 msec at a wavelength substantially above 700 nm (Gold M H, Dermatol. Surg. 1997, 23(10), 909-1). Photorejuvenation is performed at an energy density of 36 $J/cm^2$ with three pulses, while each pulse has a duration of 2.5 msec (M. B. Taylor, ASLMS Abstracts, Apr. 2001, Abstract 130). In other systems, an energy density level of 10 $J/cm^2$ is used. The angular divergence of intense pulsed light may often be a half angle of 50 degrees, or a solid angle of approximately 2 steradians, depending on the dimensions of the light guide.

Figure 2:
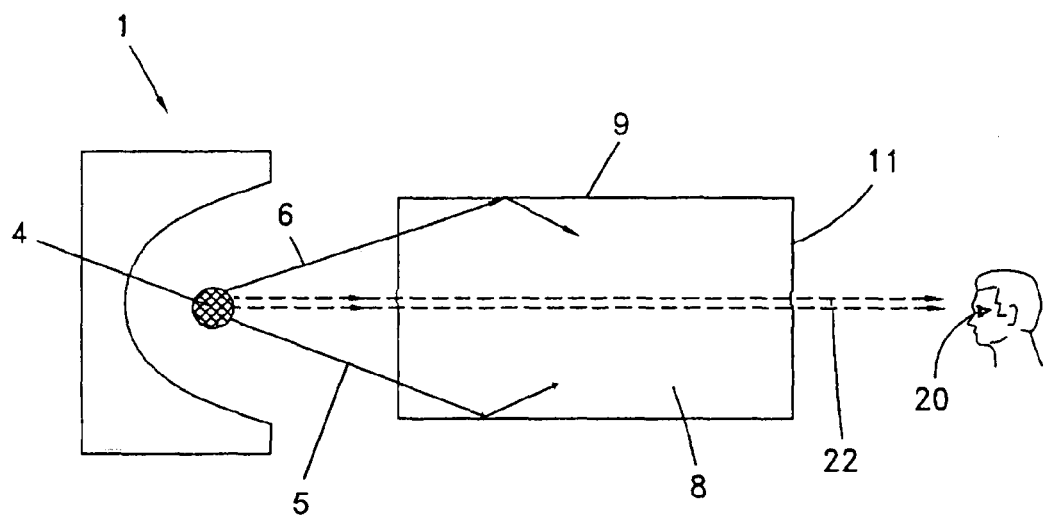
FIG. 2 is a schematic drawing which demonstrates the potential damage to an eye associated with the firing of a prior art intense pulsed light source.

Referring now to FIG. 2, potential eye injury when directly staring at prior art IPL source 1 may be demonstrated. Light rays 5 or 6 are reflected by wall 9 of light guide 8, and since they do not necessarily impinge eye 20 they are not definitively injurious to the eye. However, a direct line of sight 22 may nevertheless be established between flash lamp 4 and eye 20, causing eye 20 to be exposed to the maximum radiance of the flash lamp. The radiance of the light propagating directly from the light guide, as represented by direct line of sight 22, is much greater and more injurious than that which exits distal end 11, since the solid angle spanned by flash lamp 4 is considerably less than that spanned by distal end 11, following the reflection of light rays 5 and 6 by wall 9.

Figure 3:
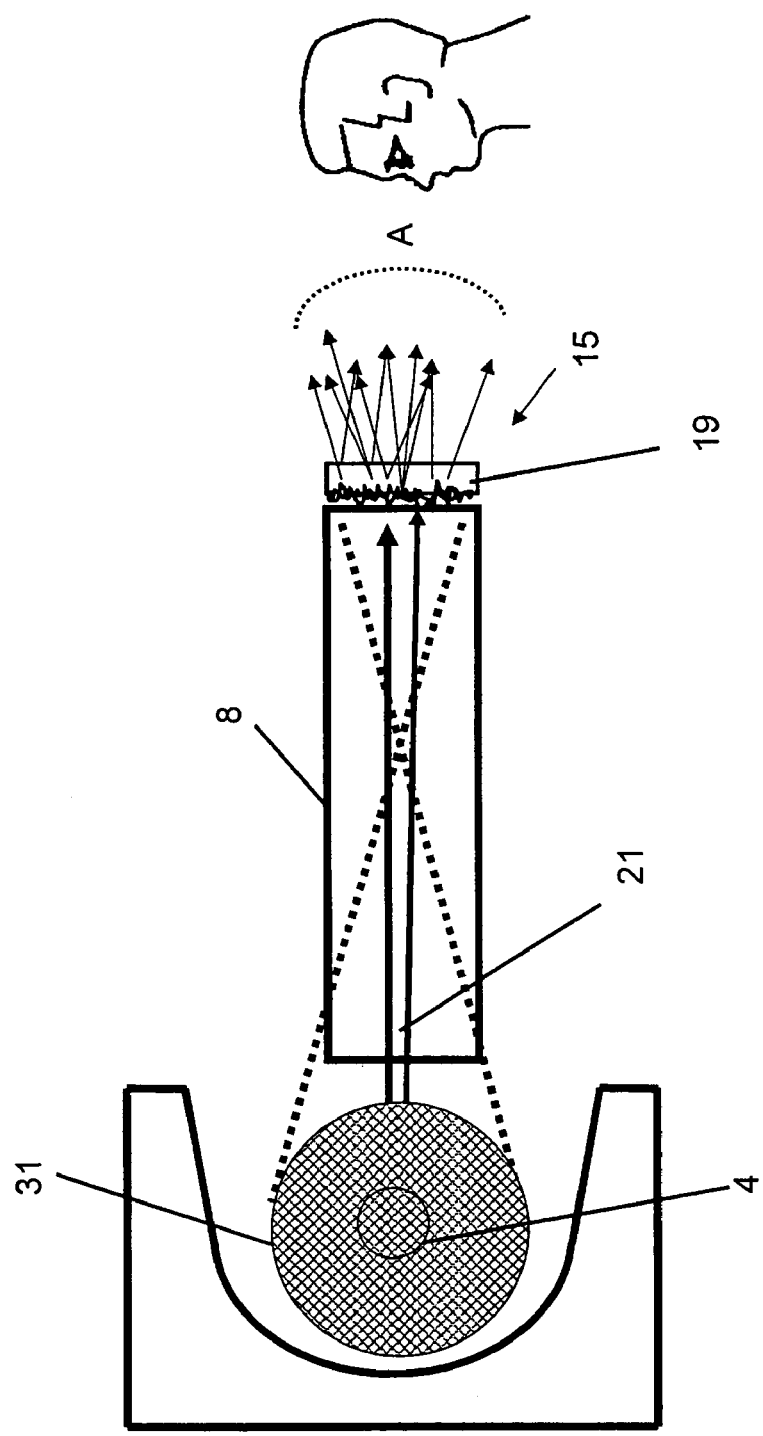
FIG. 3 is a schematic drawing of an intense pulsed light source in accordance with the present invention, showing an optical effect that results as intense pulsed light is scattered.

FIG. 3 illustrates IPL source 25, in accordance with an embodiment of the present invention. The distal end of light guide 8 is provided with diffusing unit 15 attached thereto by any means well known to those skilled in the art. The light guide may be divergent in order to increase the angular divergence of the propagating light. Diffusing unit 15 comprises diffuser 19, e.g. made of sapphire. By adding such a diffuser with a diffusing angle of A to the light guide, the image of the flash lamp is blurred on the retina and the flash lamp seems to be an enlarged extended diffusing source 31, with a width larger than flash lamp 4.

As referred to herein, "diffusing angle" is defined as the angular distribution of energy that results following the interaction of light with a diffuser, at which angle the energy density is one-tenth that of the maximum energy density of the light. A diffuser having a full angle ranging from 4 to 120 angles is suitable for the present invention.

Scattering is achieved by means of minute irregularities of a non-uniform diameter formed on the substrate of diffuser 19. Diffuser 19 is preferably produced from thin sand blasted or chemically etched glass or sapphire, e.g. having a thickness from 0.1 to 1.0 mm, or a thin sheet of non-absorbing light diffusing polymer, e.g. having a thickness of less than 500 microns, such as light diffusing polycarbonate.

Figure 4A:
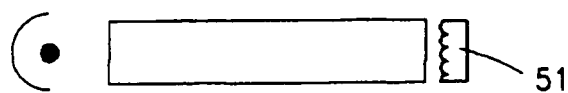
FIGS. 4a-e illustrate different configurations of diffusing units attachable to an intense pulsed light source.

A diffuser which approaches an ideal transmitting diffuser and induces a scattering half angle of 60 degrees and a scattering solid angle of 3.14 sr may be produced from material such as polycarbonate by pressing the material against an appropriate surface provided with a very dense array of Frensnel microlenses, such as those produced by Fresnel Technologies Inc., USA, or by placing arrays of microlenses surfaces separated from a light guide as depicted in FIG. 4a.

Diffuser 19 may be produced in several ways:
Sandblasting the surface of a plate of glass, sapphire, acrylic or polycarbonate with fine particles having a size ranging from 1 to 200 microns;
Sandblasting the surface of a mold plate with fine particles having a size ranging from 1 to 200 microns, comprised of, by example, aluminum oxide and reproducing the contour of the newly formed mold plate surface by pressing hot acrylic, or other suitable material thereon;
Etching the surface of a glass or sapphire plate by chemical means, such as with hydrogen fluoride;
Etching the surface of a glass plate with a scanned focused $CO_2$ laser beam; and
Applying a thin sheet of light-diffusing polymer, such as a polycarbonate sheet, to a glass plate.

Diffuser 19 is positioned such that its diffusive side faces the flash lamp, whereas its smooth side faces the skin so that any liquid such as sebum which may adhere to the diffuser will adhere to the distal smooth end thereof and will therefore not modify its diffusive properties. The diffuser may be similarly produced in other ways, such as by sandblasting, such that it conforms with FDA eye safety standard 1040.10 21 CFR Ch.1. Diffuser 19 is preferably produced from sapphire which has a high thermal conductivity, and may also be produced from other materials as well such as glass or highly durable polymers.

The AEL for visible and near-infrared radiation exiting a diffusing unit, for which protective eyeglasses are unnecessary, is based on an extended diffuser source defined by ANSI Z 136.1 as $10*k1*k2*(t^{1/3})$ J/Cm²/sr, where t is in seconds and k1=k2=1 for a wavelength of 400-700 nm, k1=1.25 and k2=1 at 750 nm, k1=1.6 and k2=1 at 810 nm, k1=3 and k2=1 at 940 nm and k1=5 and k2=1 at a wavelength of 1060 to 1400 nm.

The improved eye safety of the present invention relative to the prior art may be realized by determining the AEL associated with an exemplary IPL source—a Xenon flash lamp having a diameter of 2 mm, a length of 40 mm, an energy density of 30 J/cm², and a spectral band of 645-1100 nm, generating a pulse duration of 30 milliseconds—propagating through a light guide having a length of 120 mm and a distal end having a size of 10×40 mm.

The radiance R of the flash lamp without a diffuser, as in the prior art, is equal to the energy density of the light (30 J/cm²) divided by the solid angle spanned by the flash lamp light (π, as for any black body light source), further divided by 2, due to 50% backward light propagation and multiplied by the ratio of the width of the light guide distal end to that of the flash lamp (10:2). As a result, R=75/3.14, and is approximately equal to 24 J/cm²/sr, approximately 5 times greater than an AEL of 5 J/cm²/sr, as specified by the ANSI Z 136.1 standard for a pulse duration of 30 milliseconds.

In contrast, with the addition of a diffuser, the flash lamp diameter is blurred to a size of A×L, where A is the diffusing half angle in radians and L is the light guide length. Therefore, for a diffusing angle of 10 degrees (equal to ⅙ radians), which is typical for a chemically etched diffuser, and a light guide length of 120 mm, a blurred flash lamp diameter of 20 mm results, corresponding to a reduction in radiance by a factor of 10. As a result, the radiance of a diffused IPL source is approximately one-half of the eye-safe limit and therefore the IPL source may be operated without need of protective eyeglasses.

During treatment, the distal end of the light guide is placed on the skin target, or in close proximity thereto. Accordingly, it will be appreciated that the addition of a diffuser to the distal end of the light guide does not affect the treatment efficacy of the IPL source. The energy density of the light which impinges tissue, after being scattered by the diffuser, is substantially equal to that of the light emitted by the flash lamp, due to the proximity of the distal end of the light guide to the skin target.

Figure 4B:
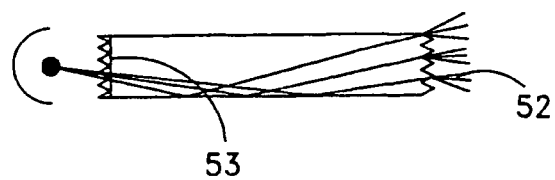
Figure 4C:
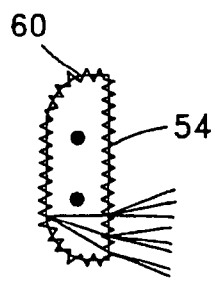
Figure 4D:
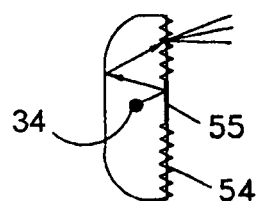
Figure 4E:
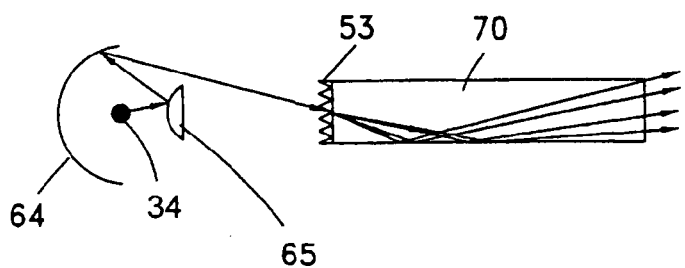

Other configurations for improving eye safety during exposure to intense pulsed light are shown in FIGS. 4a-e, in accordance with the present invention. In FIG. 4a an array of micro-lenslets 51 is employed, such as an array available from Fresnel Optics Corp. (USA), wherein each lenslet has a diameter of 0.7 mm. A micro-lenslet, as referred to herein, has a semicircular cross section, with a diameter ranging from 0.1-2.0 mm. In FIG. 4b two diffusers 52 and 53 are used. In FIG. 4c the IPL source is provided with a metallic back reflector 60, without a light guide. Back reflector 60 is etched as well as transparent distal end 54, to allow for increased scattering. In FIG. 4d a reflecting mirror 55 is installed, which conceals flash lamp 34 and prevents direct view of a high radiance zone. In FIG. 4e a pair of concave and convex reflectors 64 and 65, respectively, are used to thereby conceal flash lamp 34 and prevent staring directly at the flash lamp. Light guide 70 may be used in conjunction with the configuration of FIG. 4e to further reduce the emitted radiance. The light which exits from diffuser 53 is received by light guide 70 and is reflected within its inner wall, resulting in wide angle diffusing from the entire exit surface of the light guide. A diffusing unit may also be provided with an array of micro-lenslets, micro-prisms or a combination thereof.

Transparent skin cooling devices are often used in conjunction with skin treatments. Some skin cooling devices utilize a low temperature transparent liquid flowing across the distal end of a handpiece in contact with the skin in order to dissipate the heat generated by the IPL. Other skin chillers utilize a thermoelectric unit to chill 0074he distal end of a handpiece and to thereby transfer heat from the skin. However the prior art devices do not scatter IPL and consequently do not reduce the risks associated with eye exposure to the IPL.

Figure 5A:
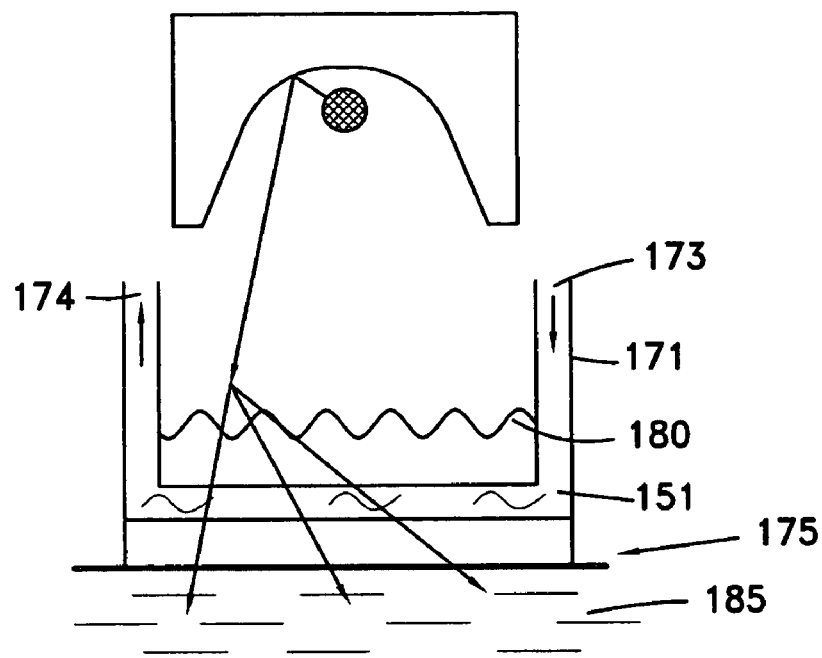
Figure 5B:
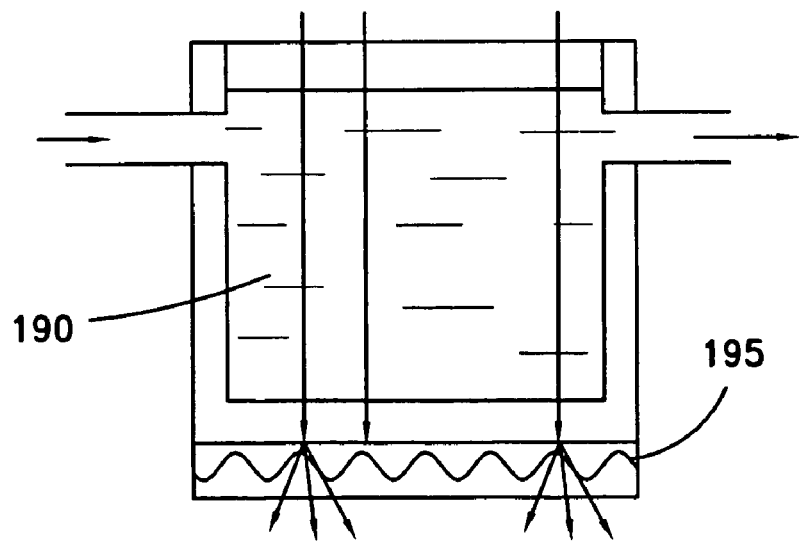

In one embodiment of the present invention, a device for scattering IPL is also provided with a cooling device. As shown in FIG. 5a, transparent cooling fluid 151, e.g. a low temperature gas or liquid of approximately 4° C., flows across diffuser 180 having a high thermal conductivity, e.g. a sapphire diffuser. Cooling fluid 151 flows through conduit 171, such that it is admitted to the cooling device at port 173 and exits therefrom at port 174. The distal end of the cooling device is in contact with skin target 185, and conducts heat from the heated skin. In FIG. 5b, cooling fluid 151 passes through vessel 190, thereby increasing its dwelling time in the vicinity of diffuser 195. In FIG. 5c thermoelectric chiller 140 chills diffuser 147, the distal end of which is in contact with skin target 185, and may also chill light guide 145.

FIGS. 6a-h illustrate another embodiment of the present invention in which a handpiece, through which light propagates from an IPL source, is provided with a liquid crystal backscattering protection unit for attenuating light backscattered from the skin, which would normally cause an operator to suffer from eye fatigue.

Operators of IPL sources are subject to long term exposure of trains of flash light pulses reflected from the skin of a patient. Although each optical pulse reflected from the skin is diffused and is not capable of burning a portion of the retina, the cumulative effect of a train of pulses results in the tiring of an eye of an operator since the pupil repetitively expands and contracts in response to the change in radiance of the light which is incident on the eyeball.

Figure 6A:
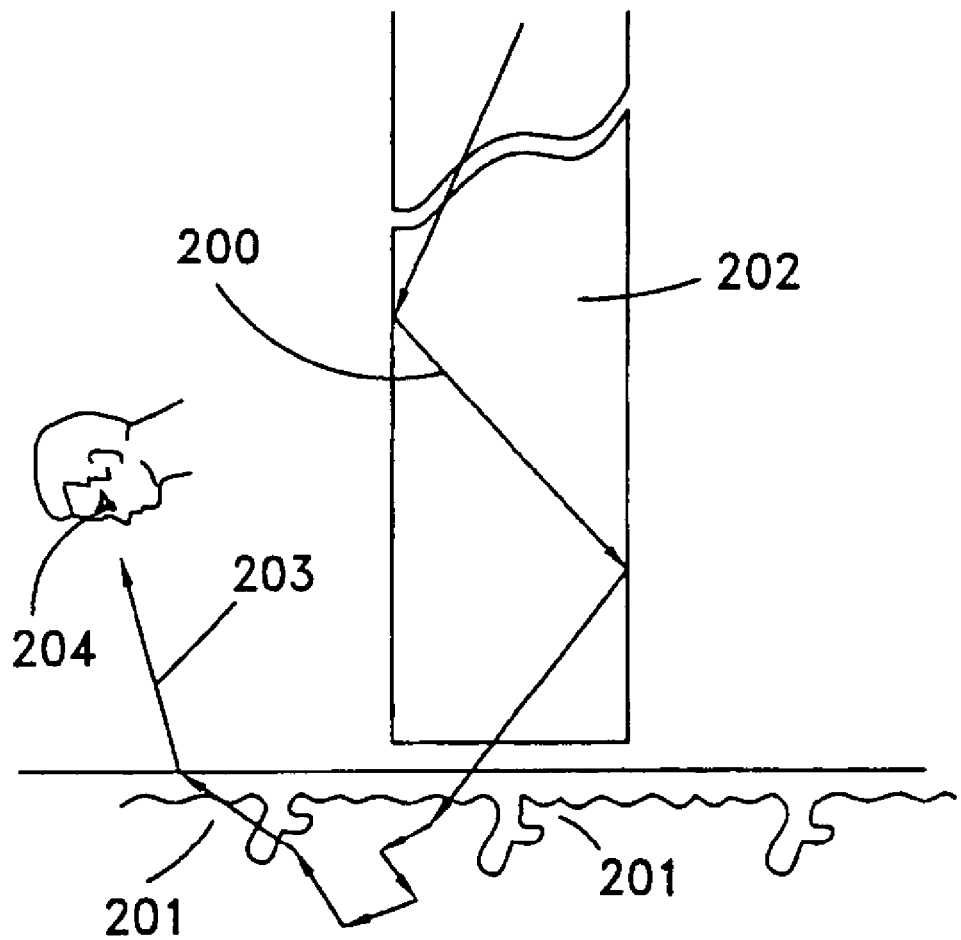
FIGS. 6a-h schematically illustrate different configurations of a backscattering protection unit.

The effect of eye tiring as a result of backscattered radiation is illustrated in FIG. 6a, wherein light guide 202 is positioned to be substantially in contact with skin 201. Light ray 200 which is reflected by the wall(s) of light guide 202 propagates through skin 201 and emerges from the skin as reflected rays 203 due to internal backscattering within the skin. Rays 203 impinge eye 1204, resulting in eye tiring after extended exposure.

Figure 6B:
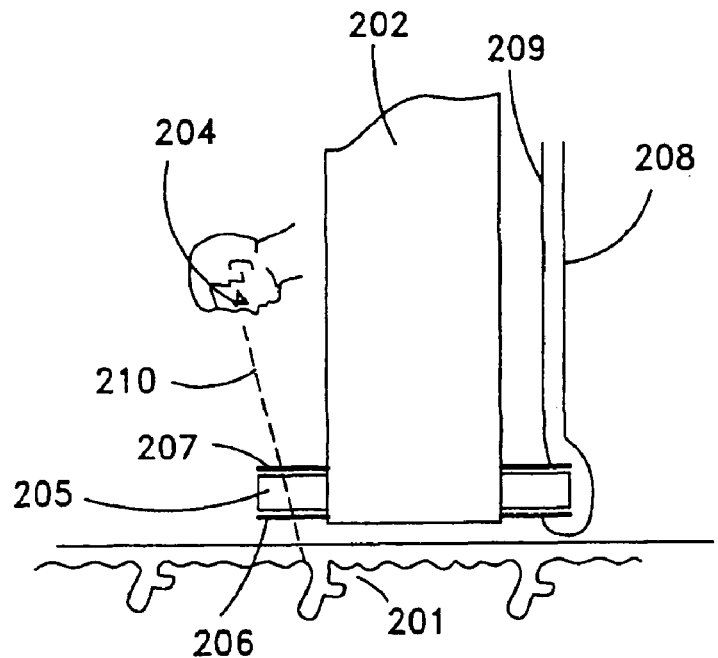

As shown in FIG. 6b, eye tiring is prevented by adding a shield around, and perpendicular to, the distal end of a handpiece of the IPL source. In the illustrated example, normally transparent liquid crystal window 205, e.g. of 2 mm thickness, is affixed to the distal end of light guide 202. When not activated, window 205 is transparent and skin 201 is visible to eye 204 by line of sight 210. Window 205 is provided with transparent electrodes 206 and 207 connected to a power supply (not shown) by wires 208 and 209, respectively.

Figure 6C:
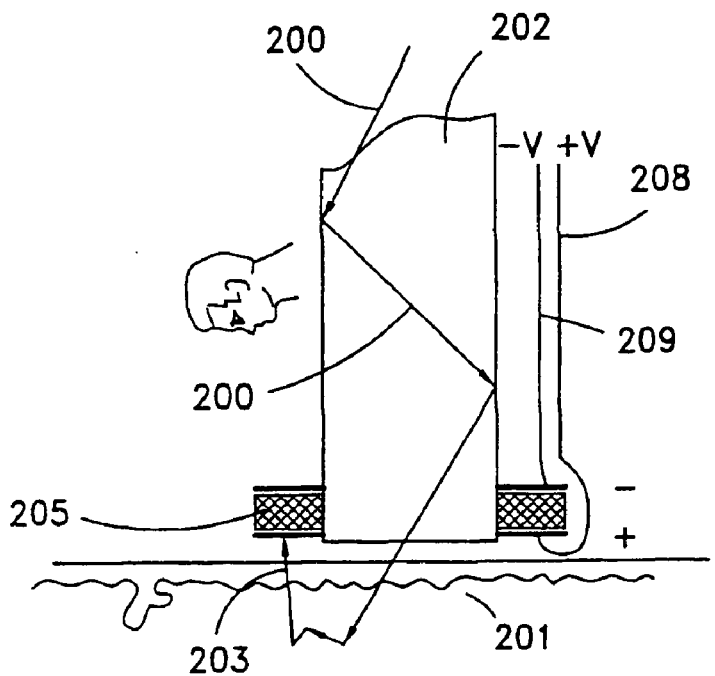

When liquid crystal window 205 becomes activated, e.g. by a low voltage of 6V, as shown in FIG. 6c, its optical properties change and the window becomes opaque to reflected ray 203. Eye 204 is no longer exposed to reflected ray 203 and eye tiring is therefore prevented. Window 205 is activated synchronously with, or shortly before, e.g. 10 msec before, the activation of a flash lamp, so that it will be opaque during the short duration of flashlight emission from the IPL source. Window 205 may be advantageously activated in accordance with a predetermined timing sequence by means of control circuitry (not shown). Since the duration of a treatment pulse is usually not longer than 300 msec and the delay between successive pulses is approximately 1-3 seconds, the short-duration opacity of the liquid crystal allows the skin to be visible during those periods when pulses are not emitted. It will be appreciated that as the transversal dimension of window 205 increases, i.e. perpendicular to the distal direction, more reflected rays will be absorbed by the liquid crystal. The transversal protrusion of one side of window 205 from light guide 202 ranges from 5-100 mm, and is preferably less than 40 mm.

Figure 6D:
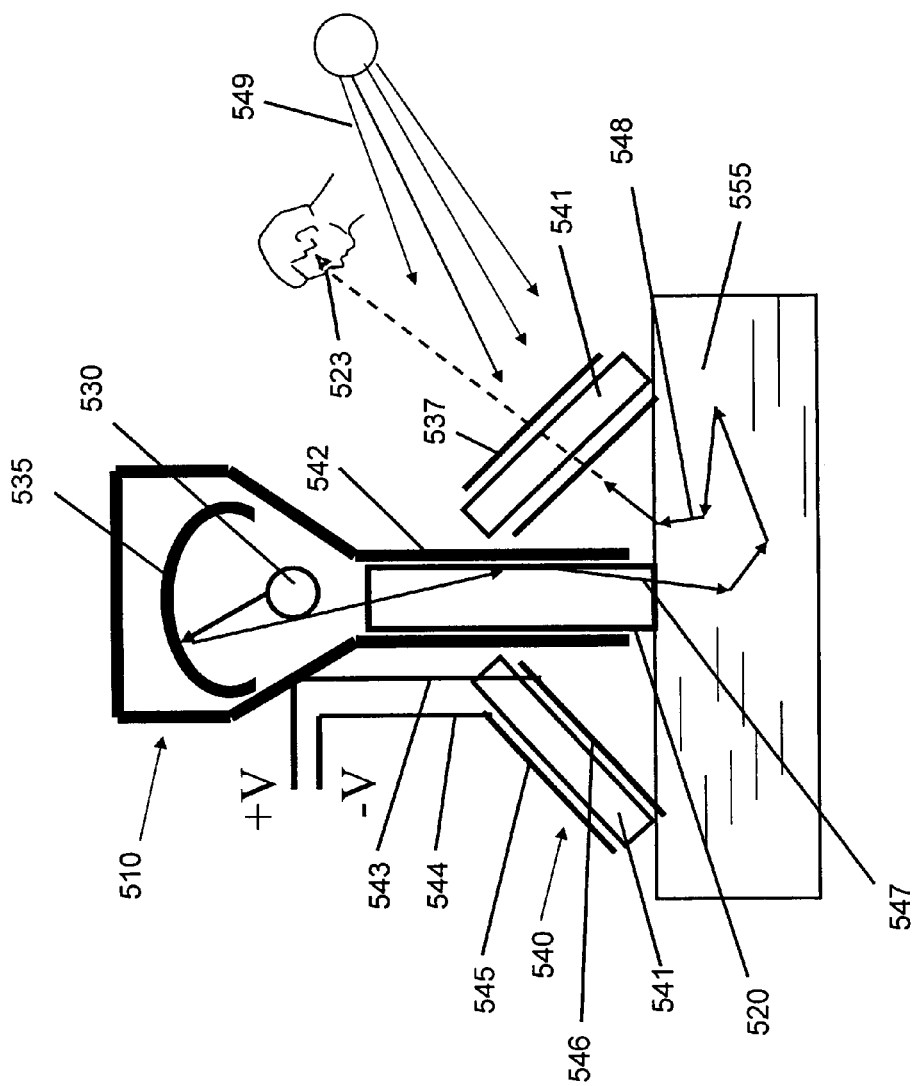

FIG. 6d schematically illustrates a device, generally indicated by numeral 510, which comprises IPL source 530 that generates light reflected by reflector 535 and propagated through light guide 520, handpiece 542, which encircles the light guide and is held in close proximity to skin target 555, and backscattering protection unit 540, which is attached externally to handpiece 542. Backscattering protection 540 may comprise a plurality of assemblies 537 that are pivotally displaceable with respect to the handpiece 542 and that house a corresponding liquid crystal window 541. Electrical wires 543 and 544 in contact with translucent conducting surfaces 545 and 546, respectively, of an assembly 537 are adapted to change the opacity of the corresponding liquid crystal window 541.

Figure 6E:
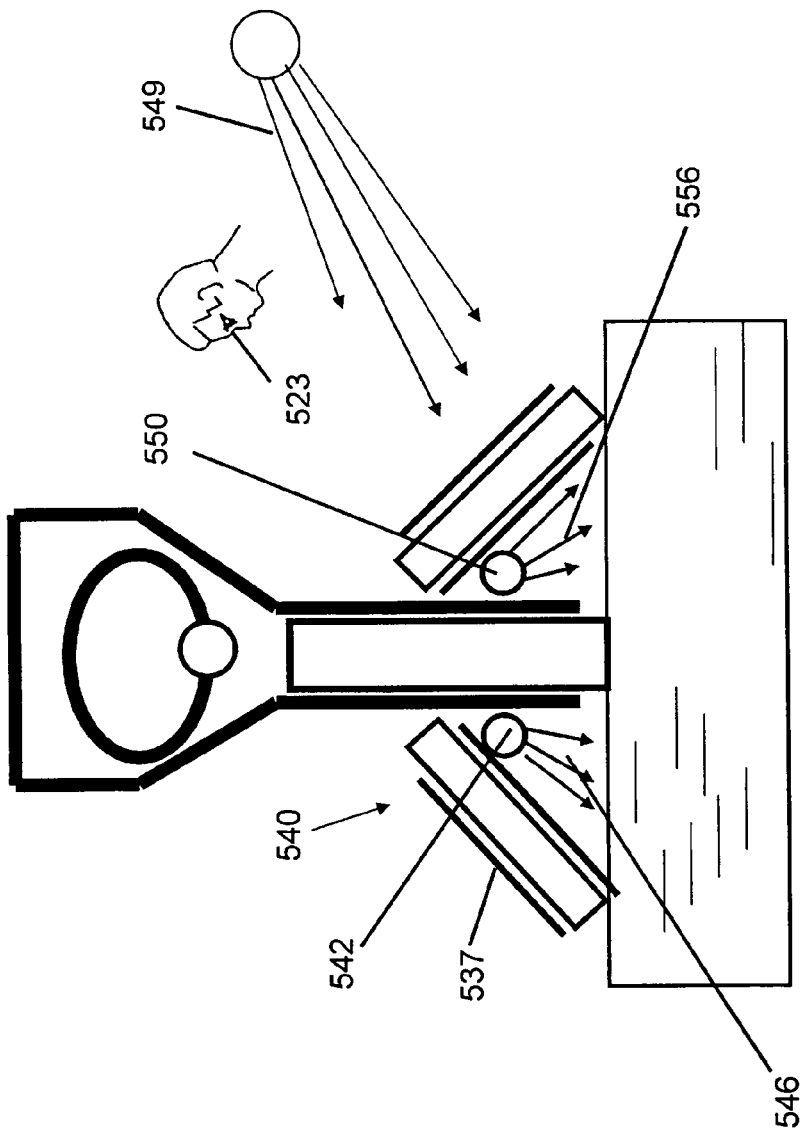

Light 547 which exits the distal end of light guide 520 and propagates through skin 555 is partially scattered, as indicated by numeral 548, by the skin and may repeatedly impinge eye 523 of an operator. By generating a potential between surfaces 545 and 546, the opacity of window 541 is increased and backscattered light 548 which propagates through the instantaneously darkened window 541 is considerably dimmed. By deactivating the potential, the transparency of window 541 is reset. Since a liquid crystal window is effectively a light polarization device, an activated window 541 dims to some extent the visibility of the treatment site which is normally illuminated by non-polarized room light 549. Room light 549 passes twice through window 541—as it propagates towards skin target 555 and as it is reflected therefrom and impinges eye 523. As shown in FIG. 6e, backscattering protection unit 540 may comprise a high intensity, miniature light source 550 for the illumination of skin 555, which is externally attached to handpiece 542 at an attachment point between assembly 537 and skin 535. Lamp 550 may emit white light, thereby compensating for the attenuation of room light 549 at skin target 555.

An exemplary liquid crystal window 541 is a homogenous analog dye guest host liquid crystal shutter produced by CRL Opto, UK, which has a response time of 20 milliseconds from an activated to deactivated state and a decay time of 70 milliseconds, and is therefore suitable for applications for which visibility cannot be impaired more than 300 milliseconds. The transition from an activated state to a deactivated state is at 3.3 V, and since the window has a sufficiently low power requirement, small Lithium batteries may in use for tens of hours of operation without replacement.

Another exemplary liquid crystal window is a matrix of liquid crystal pixels, wherein a thin-film transistor is located at each pixel intersection, requiring a relatively low amount of current to control the luminance of a pixel. The average optical transmission of the liquid crystal may therefore be varied with a wide dynamic range by switching the current through some of the transistors.

An exemplary light source 550 is a white LED, such as the "Photon Microlight II" produced by L.R.I, OR, USA, having a width of approximately 3 mm. The illumination of such a light source is maximum at a distance of a few centimeters, generating a temperature of 6500 deg Kelvin color with a sufficiently low power consumption such that two 3-Volt Lithium batteries are sufficient for over 100 hours of operation.

Figure 6F:
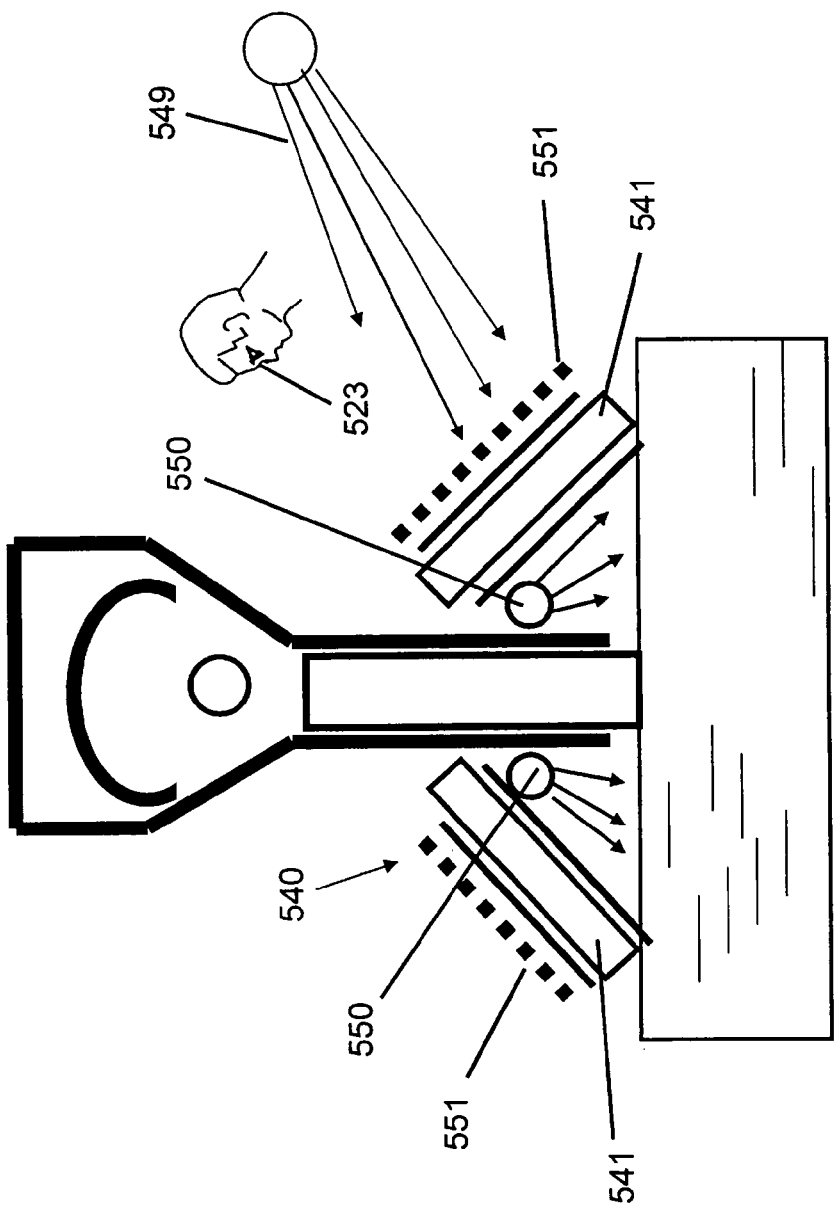

As shown in FIG. 6f, each backscattering protection unit 540 may comprise a density filter 551 in addition to liquid crystal window 541. Density filter 551, which has a predetermined constant opacity in accordance with the spectrum of the IPL, absorbs some radiation of the backscattered light, permitting only a fraction thereof to be transmitted. Density filter 551 may be advantageously employed during the generation of a very bright backscattered pulse, for which a liquid crystal window could not provide adequate attenuation, e.g. following inadvertent separation of the distal end of the handpiece from a skin target. The lack of visibility at the target skin target due to the high attenuation effected by a density filter may be compensated by increasing the illumination of the low power-consumption light source 550 upon conclusion of the firing of the IPL, e.g. after a train of pulses.

Figure 6G:
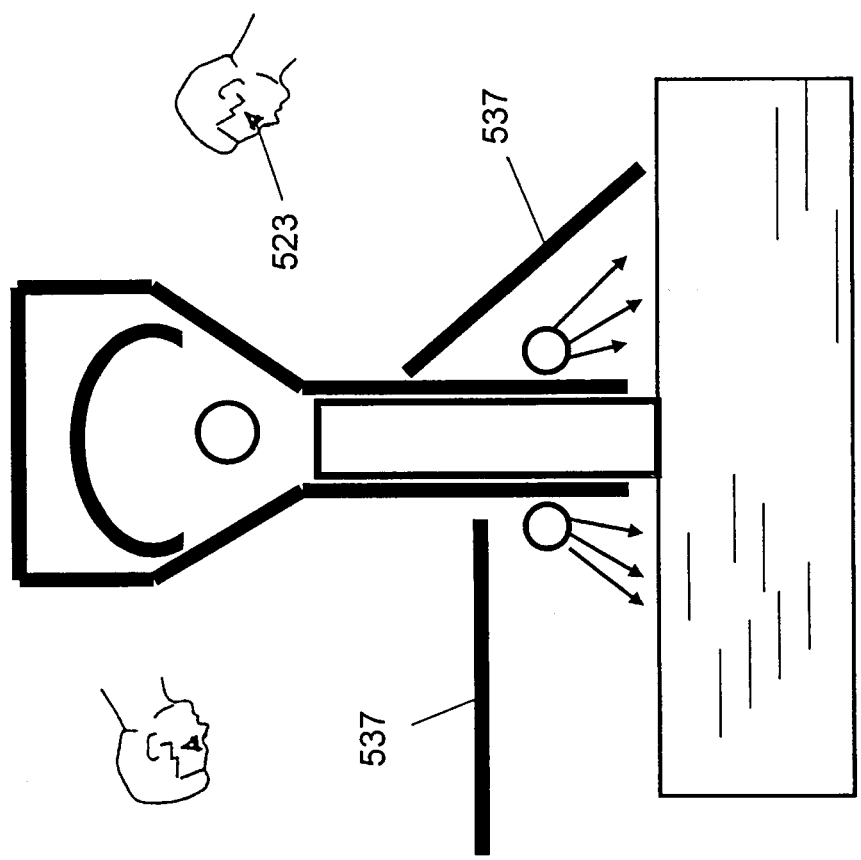

As shown in FIG. 6g, each assembly 537 provided with a liquid crystal window may be pivotally displaceable with respect to handpiece 542. The angular disposition of assembly 537 is adjustable, so as to provide optimal protection to eye 523, as the operator changes position, for example, from a sitting to a standing position, or moves side to side.

Figure 6H:
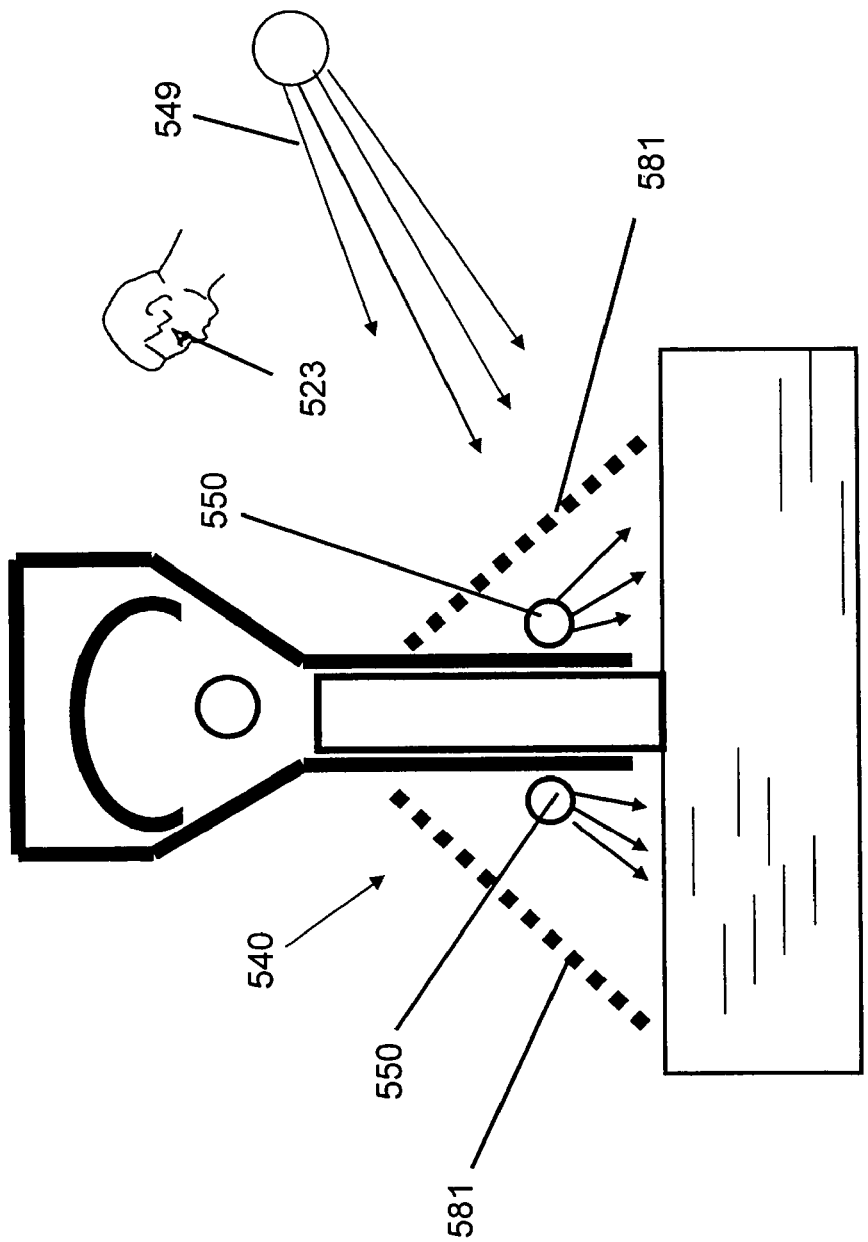

As shown in FIG. 6h, backscattering protection unit 540 may comprise eye protection shield 581, e.g. having a conical shape, which may be used for several applications such as for hair removal. Shield 581 may be a low cut-off filter at the invisible 810 nm wavelength, i.e. is adapted for filtering backscattered IPL at a wavelength longer than 810 nm. Light at a wavelength longer than 810 nm is suitable for treating hair without damaging the epidermis. If the optical transmission of shield 581 at a wavelength below 810 nm is high, the illumination of room light 549 may be sufficiently high so as to provide adequate visibility at the skin target. However, if the room illumination is not sufficiently high, light source 550 may supplement the illumination.

Figure 7:
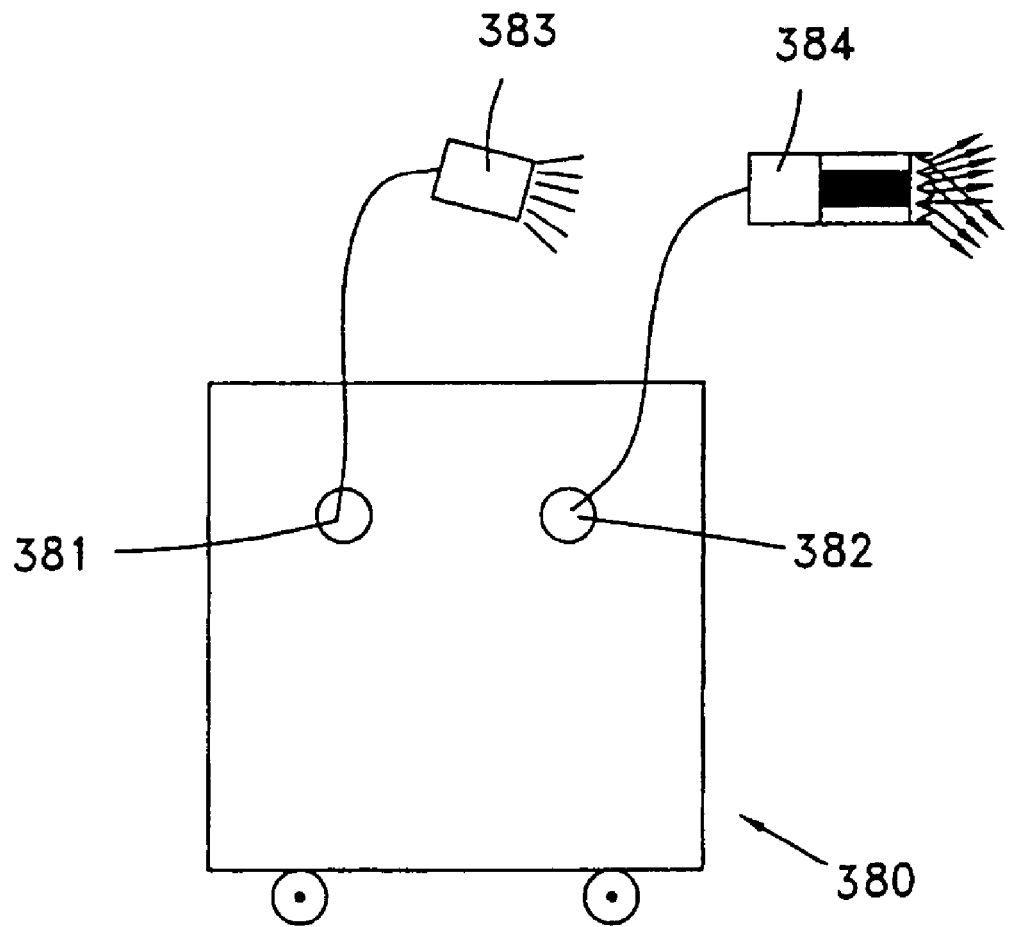
FIG. 7 is a schematic drawing of a dual laser and IPL generator, in accordance with the present invention.

FIG. 7 illustrates a dual system for aesthetic treatments. Dual system 380 incorporates a power supply which can energize both an IPL source 383, which is insertable through port 381, and laser source 384, which is insertable through port 382. Each of the IPL source 383 and laser source 384 is provided with a diffusing unit at the corresponding distal end so that the light which exits therefrom is eyesafe to a bystander. Co-pending International Patent Publication WO 03/049633 by the same applicant, describes an eye-safe laser unit suitable for aesthetic treatments, wherein a diffusing unit is attached to the distal end of the laser source. Similarly other configurations for converting highly risky monochromatic laser units, which are suitable for aesthetic treatments, into non-coherent, eye-safe units are described therein.

It will be appreciated that the employment of one of the aforementioned diffusing units, which is attachable to the distal end of a laser source or an IPL source for effecting an aesthetic improvement by directing the generated light to a skin target, has an additional advantage of preventing the generation of subcutaneous microscopic hot spots, which are often the cause for adverse side effects such as the occurrence of purpura during the treatment of vascular lesions or of scarring during the treatment of wrinkles.

The prior art treatment of vascular lesions with a Dye laser, for example, requires an energy density level ranging from 8-14 J/cm$^2$ and a pulse duration of approximately 300 microseconds. Upon exiting the propagation assembly, particularly following impingement of the upper skin surface, such a generated laser beam partially scatters and the coherence thereof gradually disappears. As the exiting laser beam partially scatters, the coherence of the beam results in constructive interference, causing the formation of interference speckles having a local energy density level as high as approximately 2-3 times the average energy density of surrounding skin regions. Hot spots coinciding with these interference speckles are microscopic in size, e.g. a diameter of a few microns, and invisible to a bare eye. Although the beam seems homogeneous to a bystander, the partial scattering thereof causes severe purpura as a result of the excessive destruction of blood vessels of the size of the speckles. Purpura is known to be a significant adverse side effect resulting from the treatment of port wine stain.

By placing one of the diffusing units shown in FIGS. 4a-d in contact with the skin, the treatment beam is completely scattered and homogenized below the upper skin surface. Since coherence of the laser beam is completely destroyed by means of the diffusing unit, high intensity speckles result, each of which having a size considerably smaller than that of the neighboring blood vessels. Consequently, essentially purpura-free laser-based aesthetic treatments may be effected.

To illustrate this inventive feature, FIG. 10a illustrates collimated beam 2000 which is emitted from fiber 2001, impinging skin target 2008 and producing spot 2002 thereon. Due to the partial scattering of beam 2000, interference speckles result. When blood vessel 2004 is impinged by the laser beam, interference speckles 2003 are formed within spot 2002, causing the appearance of purpura, while the average energy density of skin regions adjacent to speckles 2003 is considerably less. By the addition of a diffuser 2005 as shown in FIG. 10b, beam 2000 is homogenized as it propagates through skin target 2008. Blood vessel 2004 is subsequently homogeneously treated and unaffected by interference speckles, and spot 2002 remains purpura-free.

Hot spots may also be generated during the operation of an IPL. When a flash lamp is placed on, or extremely close to, a skin target, as carried out with use of the IPL source manufactured by Deka, Italy, the current flowing to the arc which powers the lamp is not uniform. Consequently, the flash lamp discharge is not uniform, causing inhomogeneous reflection into the skin which may result in hot spot formation. The attachment of a diffuser to an IPL operating in the 570-645 nm spectral band therefore also provides a purpura-free treatment of vascular lesions.

Co-pending U.S. patent application Ser. No. 10/498,382 by the same applicant discloses an additional method and apparatus for preventing the appearance of purpura, by which a controlled vacuum is applied to a vacuum chamber in contact with a skin target, so that a significantly lower energy density level relative to prior art methods is sufficient for achieving the coagulation of blood vessels.

EXAMPLE 1

Figure 8:
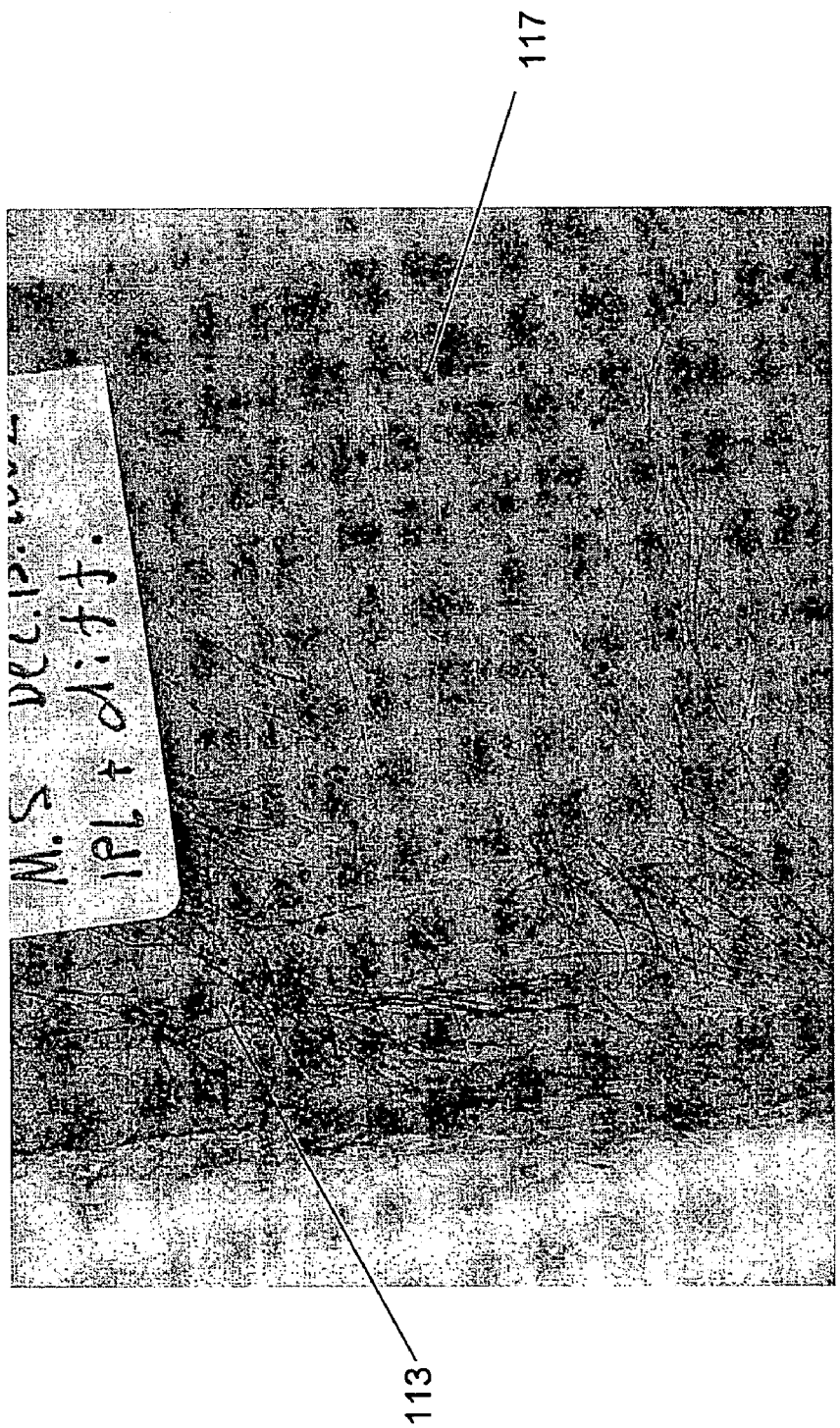
FIG. 8 is a picture of an arm of the patient, illustrating the efficacy of diffused intense pulsed light, in accordance with the present invention.

FIG. 8 illustrates the efficacy of diffused intense pulsed light, according to the present invention.

A single IPL pulse having an energy density of 20 $J/cm^2$ and a pulse duration of 20 milliseconds was directed at an arm 113 of a patient having a hair density of approximately 40 $hairs/cm^2$. A sapphire diffuser, which was thermoelectrically chilled to a temperature of approximately 4° C., with a diffusing angle of 10 degrees was attached to the distal end of the light guide of the IPL source. A cut-off spectral filter with a surface area of 8×40 mm, which transmits light at a wavelength longer than 750 nm, was attached externally to the handpiece of the IPL source.

The arm of the patient was marked with a plurality of dots 117 to indicate the skin target at which the IPL was to be directed, an area of 8×40 mm. The pulse of IPL light was fired on Oct. 27, 2002 and the shown picture was taken on Dec. 15, 2002, at which time the hair density within the treatment zone was less than 4 $hairs/cm^2$. The hair density in the untreated zone was equal to the hair density within the treated zone before the treatment. It can be seen that an IPL source provided with a diffusing unit at the distal end thereof is efficacious for hair removal.

The addition of a diffusing unit can be equally effective for other applications. A spectral band greater than 550 nm can be utilized for the treatment of vascular lesions, greater than 400 nm for the treatment of acne, greater than 750 for hair removal of subjects with dark skin, and greater than 550 nm for photorejuvenation.

Figure 9B:
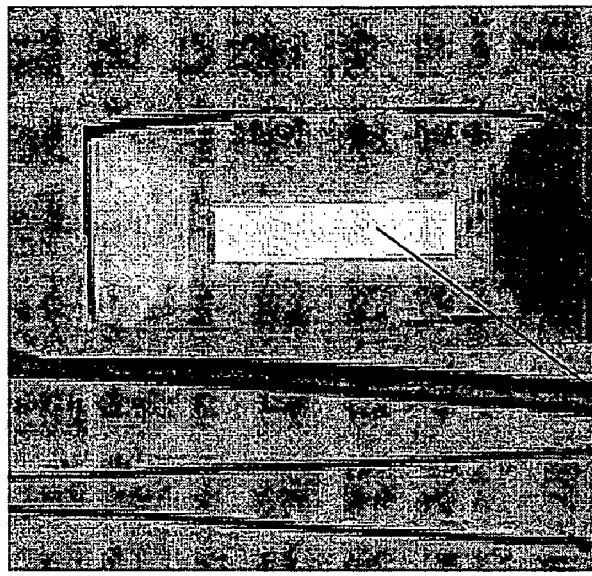
FIGS. 9a-b are pictures of the distal end of an intense pulsed light source without and with a diffuser, respectively, showing the lowered radiance that may be realized with the use of the present invention.
Figure 9A:
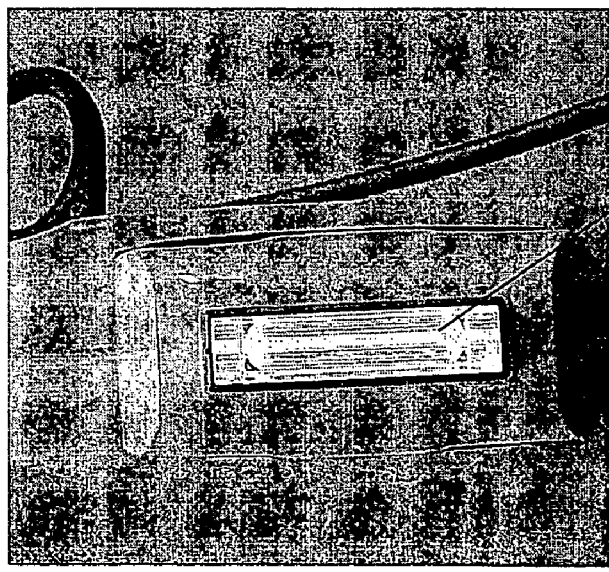

FIGS. 9a and 9b are pictures of the distal end of the IPL source used for the aforementioned treatment without and with a 10 degrees sapphire diffuser, respectively. A blinding flash lamp 30 is seen in FIG. 9a, whereas the addition of diffuser 32 resulted in a safe low-radiance, extended diffusing surface, as shown in FIG. 9b. A filter was added to the camera before the picture of FIG. 9a was taken, so as to ensure camera integrity, and it will be appreciated that the radiance emitted by flash lamp 30 was much greater than the light that exited diffuser 32.

EXAMPLE 2

A small-sized IPL source, which generated a relatively low energy density of 5 $J/cm^2$, can be used as a shaver for home use, necessitating shaving only once in two weeks.

The operator may place a handpiece having a width of 3 cm and a length of 5 cm on his own face. After the operator depresses the activation switch located on the handpiece with his thumb, he may shave his face with IPL while viewing his reflection in a mirror, without need of protective eyeglasses.

A Xenon flash lamp, which has a diameter of 1 mm and a length of 20 mm, with a spectral emission of 550 nm, thereby being greatly absorbed by melanin, may be employed. One fired pulse may remove facial hair from an area of 4×20 mm. The pulse duration may be 3 milliseconds, to ensure efficacy at the low energy density 5 $J/cm^2$, and the pulse repetition rate may be once in 3 seconds. The face of the operator may be completely shaved within 3 minutes.

A sapphire diffuser having a half-angle of 10 degrees may be attached to the distal end of the handpiece, at a distance of 12 mm from the flash lamp. With the aforementioned parameters, the flash lamp diameter will appear to be 2 mm and the radiance will be equal to AEL, a value of approximately 2 $J/cm^2/sr$ for a pulse duration of 3 milliseconds. Therefore shaving could be safely conducted without needing protective eyeglasses. The IPL will not be injurious to the eyes of the operator, even when the handpiece is separated from his face during the firing of the light.

As can be seen from the above description, a diffusing/diverging unit of the present invention, which is mounted to the exit aperture of an intense pulsed light source induces the exiting light to be divergent and/or scattered at a wide angle. As a result, the exiting light has a small enough radiance not to be injurious to the eyes of observers which may accidentally stare directly at the hand piece. Nevertheless, the exiting light generally retains a similar level of energy density as the light generated from the exit aperture when the diffusing/diverging unit is very close or essentially in contact with the target, and is therefore capable of performing various types of treatment while preventing the appearance of purpura or of scarring. Protective eyeglasses are generally not needed, particularly since a backscattering protection unit is added to the handpiece, and therefore an IPL source may be operated in an aesthetic clinic or even in one's home by personnel without any medical training, in a less cumbersome and safer way than which was known heretofore.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. An apparatus for treating a skin target, the apparatus comprising:
    a light source adapted to generate eye-hazardous polychromatic light with a radiance that is more than $10*k1*k2*(t^{1/3})$ J/cm$^2$/sr, where k2=1 and t is a pulse duration of the eye-safe polychromatic light in seconds, k1=1 for a wavelength ranging from 580 to 700 nm, k1=1.3 for a wavelength of approximately 570 nm, k1=1.6 for a wavelength of approximately 830 nm, k1=3 for a wavelength of approximately 940 nm, and k1=5 for a wavelength greater than 1050 nm having a source energy density sufficient to treat a skin target;
    a light guide adapted to deliver the eye-hazardous polychromatic light from the light source to a distal end of the light guide; and
    a diffusing unit attachable to the distal end of the light guide and configured to contact the skin target, the diffusing unit configured (i) to receive the eye-hazardous polychromatic light from the light guide and deliver to the skin target the eye-hazardous polychromatic light having an energy density substantially equal to the source energy density when the diffusing unit is in contact with the skin target and (ii) to receive the eye-hazardous polychromatic light from the light guide and deliver at a distance from the diffusing unit eye-safe polychromatic light with a radiance that is less than $10*k1*k2*(t^{1/3})$ J/cm$^2$/sr having a second energy density substantially less than the source energy density when the diffusing unit is spaced from the skin.

2. The apparatus according to claim 1 the eye-hazardous polychromatic light has a wavelength and the energy density which is suitable for effecting a desired treatment of the skin target without formation of purpura in a vicinity of the skin target.

3. The apparatus according to claim 1 wherein the light source is capable of generating the eye-hazardous polychromatic light having a wavelength of approximately 570-900 nm.

4. The apparatus of claim 1 wherein the diffusing unit comprises an angular beam expander, a micro-prism, a diffuser, or any combination thereof.

5. The apparatus of claim 1 further comprising a coupler disposed at the distal end of the light guide.

6. The apparatus of claim 1 wherein the light source is capable of generating eye-hazardous polychromatic light having the source energy density of approximately 1 to 100 J/cm$^2$, a pulse duration of approximately 100 microseconds to 1000 milliseconds, and a wavelength of approximately 400 nm to approximately 1300 nm.

7. The apparatus of claim 1 further comprising a skin cooling unit adapted to cool the diffusing unit.

8. The apparatus of claim 1 wherein the diffusing unit comprises sapphire, glass, or polycarbonate.

9. The apparatus of claim 1 wherein the diffusing unit comprises a first diffusing face and a second smooth diffusing face in opposed relation to the first diffusing face.

10. The apparatus of claim 1 wherein the light source is an intense-pulsed light source.

11. The apparatus of claim 1 wherein the eye-safe polychromatic light has a radiance less than an accessible emission limit.

12. An apparatus for treating a skin target, the apparatus comprising:
    a light source adapted to generate eye-hazardous polychromatic light having a radiance of more than an accessible emission limit and a source energy density sufficient to treat a skin target;
    a light guide adapted to deliver the eye-hazardous polychromatic light from the light source to a distal end of the light guide; and
    a diffusing unit attachable to the distal end of the light guide and configured to contact the skin target, the diffusing unit configured (i) to receive the eye-hazardous polychromatic light from the light guide and deliver to the skin target the eye-hazardous polychromatic light having an energy density substantially equal to the source energy density when the diffusing unit is in contact with the skin target and (ii) to receive the eye-hazardous polychromatic light from the light guide and deliver at a distance from the diffusing unit eye-safe polychromatic light having a radiance of less than the accessible emission limit and a second energy density substantially less than the source energy density when the diffusing unit is spaced from the skin; and a backscattering unit attached to the light guide and having an opacity, the backscattering unit positioned to absorb substantially all of the eye-hazardous and the eye-safe polychromatic light backscattered from the skin target.

13. The apparatus of claim 12 wherein the opacity of the backscattering unit is adjustable depending on the eye-hazardous polychromatic light generated by the light source.

14. The apparatus of claim 12 wherein the opacity of the backscattering unit increases upon generation of the eye-hazardous polychromatic light by the light source.

15. The apparatus of claim 12 wherein the backscatter unit comprises a liquid crystal window, a spectral density filter, an attenuation filter, a mechanical shutter, or a combination thereof.

16. The apparatus of claim 15 wherein the attenuation filter is an optical band pass filter.

17. The apparatus of claim 12 wherein the opacity of the backscatter unit is a predetermined constant value selected based on a spectrum of the eye-hazardous polychromatic light.

18. The apparatus of claim 12 further comprising control circuitry for synchronizing the opacity of the backscatter unit in response to the generation of the eye-hazardous polychromatic light.

19. An apparatus to improve bodily safety of bystanders exposed to eye-hazardous polychromatic light, the apparatus comprising:
    means for generating the eye-hazardous polychromatic light having a source energy density sufficient to treat a skin target;
    means for delivering the eye-hazardous polychromatic light; and
    means for (i) receiving the eye-hazardous polychromatic light with a radiance that is more than $10*k1*k2*(t^{1/3})$ J/cm$^2$/sr, where k2=1 and t is a pulse duration of the eye-safe polychromatic light in seconds, k1=1 for a wavelength ranging from 580 to 700 nm k1=1.3 for a wavelength of approximately 570 nm, k1=1.6 for a wavelength of approximately 830 nm, k1=3 for a wavelength of approximately 940 nm, and k1=5 for a wavelength greater than 1050 nm from the light guide and delivering to the skin target the eye-hazardous polychromatic light having a first energy density substantially equal to the source energy density when the diffusing unit is in contact with the skin target and (ii) receiving the eye-hazardous polychromatic light from the light guide and delivering eye-safe polychromatic light with a radiance that is less than $10*k1*k2*(t^{1/3})$ J/cm$^2$/sr and having a second energy density substantially less than the source energy density when the diffusing unit is spaced from the skin target.

* * * * *